(12) United States Patent
Miller et al.

(10) Patent No.: US 7,471,382 B2
(45) Date of Patent: Dec. 30, 2008

(54) SURFACE INSPECTION SYSTEM WITH IMPROVED CAPABILITIES

(75) Inventors: Lawrence Robert Miller, Los Altos, CA (US); Mehdi Vaez-Iravani, Los Gatos, CA (US)

(73) Assignee: KLA-Tencor Technologies Corporation, Milpitas, CA (US)

(*) Notice: Subject to any disclaimer, the term of this patent is extended or adjusted under 35 U.S.C. 154(b) by 259 days.

(21) Appl. No.: 11/243,349

(22) Filed: Oct. 3, 2005

(65) Prior Publication Data

US 2006/0109457 A1 May 25, 2006

Related U.S. Application Data

(60) Provisional application No. 60/615,918, filed on Oct. 4, 2004.

(51) Int. Cl.
*G01N 21/00* (2006.01)

(52) U.S. Cl. .................. 356/237.4; 356/237.5
(58) Field of Classification Search ......... 382/144–147; 356/237.1–237.5; 250/559.01–559.09
See application file for complete search history.

(56) References Cited

U.S. PATENT DOCUMENTS

| | | | |
|---|---|---|---|
| 5,864,394 A * | 1/1999 | Jordan et al. | 356/237.2 |
| 6,166,393 A * | 12/2000 | Paul et al. | 250/559.08 |
| 6,201,601 B1 | 3/2001 | Vaez-Iravani et al. | |
| 6,215,551 B1 | 4/2001 | Nikoonahad et al. | |
| 6,271,916 B1 | 8/2001 | Marxer et al. | |
| 6,496,256 B1 | 12/2002 | Eytan et al. | |
| 6,538,730 B2 | 3/2003 | Vaez-Iravani et al. | |
| 2002/0051130 A1* | 5/2002 | Marxer et al. | 356/237.3 |
| 2004/0036863 A1 | 2/2004 | Matsusita et al. | |
| 2004/0042001 A1* | 3/2004 | Vaez-Iravani et al. | 356/237.2 |
| 2005/0018181 A1* | 1/2005 | Vaez-Iravani et al. | 356/237.1 |

FOREIGN PATENT DOCUMENTS

DE    4134747 A1    4/1993

OTHER PUBLICATIONS

Notification Of Transmittal Of The International Search Report And The Written Opinion Of The International Searching Authority for International Application No. PCT/US2005/035867, Date of Mailing Mar. 27, 2006, 11 pages.
Gottlieb, "Acoustooptic Scanners and Modulators", Optical Scanning, Dekker 1991, pp. 615-685.
Hackerott, Semiconductor Wafermap Mathematics, May 9, 2001, 11 pages.

* cited by examiner

*Primary Examiner*—Michael A Lyons
*Assistant Examiner*—Tri T Ton
(74) *Attorney, Agent, or Firm*—Davis Wright Tremaine LLP

(57) ABSTRACT

Pixel intensities indicative of scattered radiation from portions of the inspected surface surrounding a location of a potential anomaly are also stored so that such data is available for quick review of the pixel intensities within a patch on the surface containing the location of the potential anomaly. Where rotational motion is caused between the illumination beam and the inspected surface, signal-to-noise ratio may be improved by comparing the pixel intensities of pixels at corresponding positions on two different surfaces that are inspected, where corresponding pixels at the same relative locations on the two different surfaces are illuminated and scattered radiation therefrom collected and detected under the same optical conditions.

18 Claims, 15 Drawing Sheets

Convergent Hollow Cone of Light

A Possible Arrangement of Multiple Fiber Channels

Segmented Fiber Channels

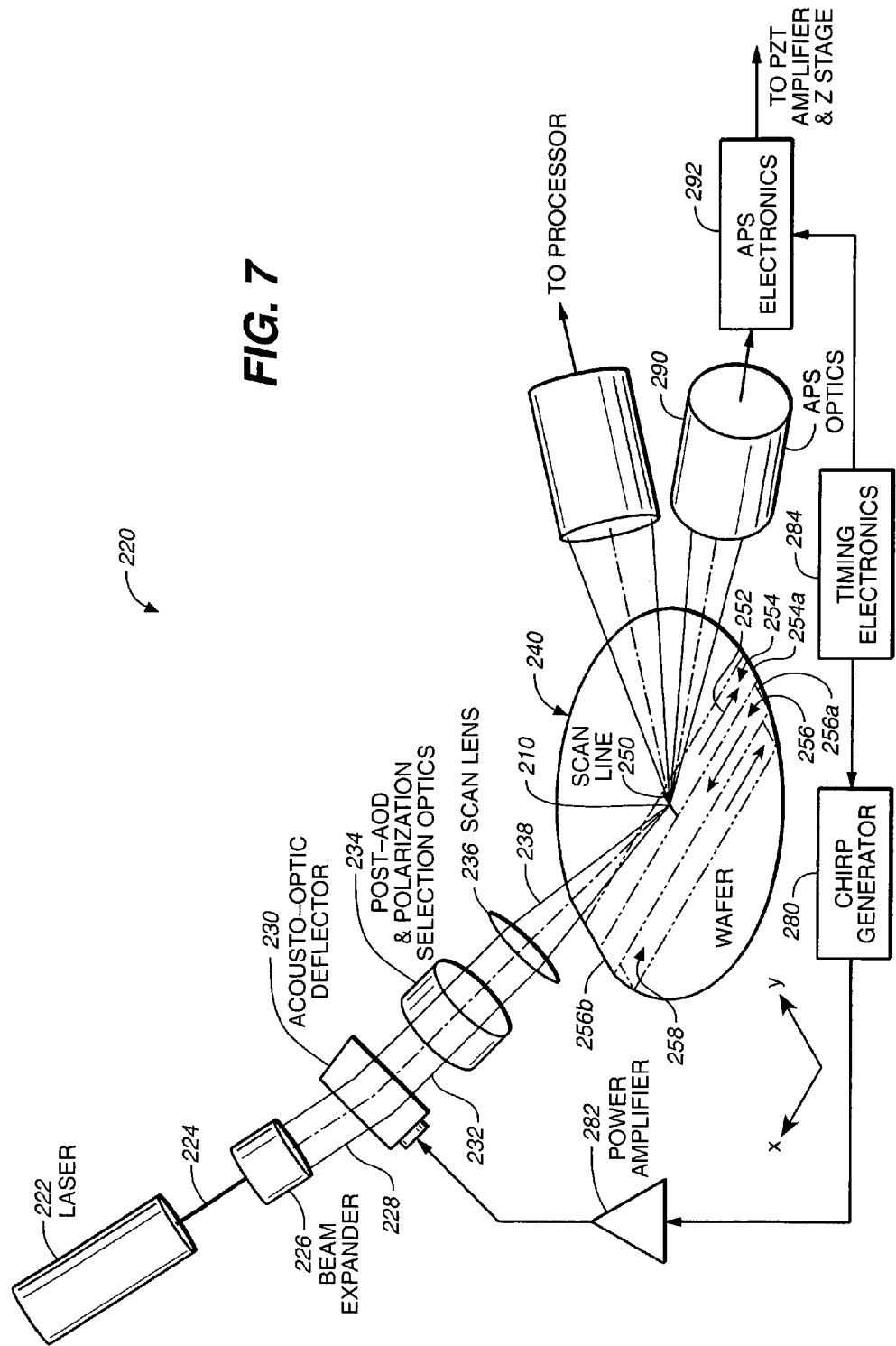

FIG. 11

SURFACE INSPECTION SYSTEM WITH IMPROVED CAPABILITIES

CROSS-REFERENCE TO RELATED APPLICATIONS

This application claims the benefit of U.S. Provisional Application No. 60/615,918, filed Oct. 4, 2004, which application is incorporated by reference as if fully set forth herein.

BACKGROUND OF THE INVENTION

This invention relates in general to defect detection, and, in particular, to an improved system for detecting anomalies on surfaces, such as particles and surface-originated defects such as crystal-originated particles ("COPs") and other defects.

The Sp1$^{TBI}$™ detection system available from KLA-Tencor Corporation of San Jose, Calif., the Assignee of the present application, is particularly useful for detecting defects on unpatterned semiconductor wafers. The SP1$^{TBI}$ system provides the capability to review areas of the surface where potential anomalies have been identified, in a mode known as microview. The SP1$^{TBI}$ system determines the presence of potential anomalies by comparing intensities of detector outputs with a threshold. If the intensity of radiation detected by the detector exceeds the threshold, a potential anomaly is then determined to be present at the location from which the scattered radiation is detected. The intensity value is then stored and identified to be indicative of a potential anomaly at a corresponding location of the surface.

After the entire surface (such as the surface of a semiconductor wafer, reticle or display panel) has been inspected in this manner, the areas containing locations where the potential anomalies are found are then re-examined to determine whether anomalies are actually present at such locations. In this determination, it is useful and often necessary to compare the radiation scattered by the surface at the locations determined to have potential anomalies to radiation scattered by portions of the surface surrounding such locations, such as portions within patches or areas of the surface, each patch or area containing one of such locations. In the microview mode, the SP1$^{TBI}$ system re-scans the portions of the surface surrounding the locations determined to have potential anomalies, and records the detector output intensities so obtained. This is necessary because the scattered radiation intensities detected by the detectors from areas surrounding the potential anomalies (and where no potential anomaly has been detected) fall below the threshold and are therefore discarded and not stored. A comparison of the detector output intensities of radiation scattered by the surface at the locations determined to have potential anomalies to the detector output intensities of radiation scattered by portions of the surface surrounding such locations will confirm whether anomalies are indeed present at such locations. These confirmed locations with potential anomalies can then be examined in greater detail or at higher resolution. The microview mode is useful since there may be a large number of locations with potential anomalies, and the re-scanning and comparison process in this mode may reduce the number of locations that would need to be examined in greater detail or at higher resolution.

While the above-described microview mode of the SP1$^{TBI}$ system is useful, it requires re-scanning of the surface. The SP1$^{TBI}$ system provides unsurpassed defect sensitivity on bare wafers or unpatterned wafers; however, this is not the case when it is used for inspecting wafers with patterns thereon such as wafers with memory arrays, or for inspecting surfaces with much back ground noise.

Where rotational motion is caused between the illumination beam and the surface that is being inspected, it may be difficult to perform what is known as die-to-die comparison between pixel intensities of two different areas on the same surface that is being inspected. This is due to the fact that the angle of illumination of the two areas may be different, since the areas may be illuminated at different azimuthal angles, and the collection angles (both azimuthal and elevation) of scattered radiation may also differ between the two areas, depending on the timing of the rotation. If the two areas contain pattern, the pattern then may be at different orientations relative to the illumination beam and the collection optics so that a subtraction of the pixel intensities of the two areas or patches does not normally reduce noise caused by scattering due to pattern.

It is therefore desirable to provide a surface inspection system with capabilities that are better than those outlined above.

SUMMARY OF THE INVENTION

This invention is based on the recognition that the above-described difficulties encountered in the microview mode of the SP1$^{TBI}$ system can be overcome by storing, in addition to information concerning radiation scattered from locations of the surface determined to have potential anomalies, also information concerning radiation scattered from portions of the surface adjacent to such locations and not determined to have potential anomalies. This is in contrast to the current microview mode of the SP1$^{TBI}$ system where only the intensities of the radiation scattered from locations of the surface determined to have potential anomalies are stored. In this manner, subsequent to the scan, if the user desires to view radiation scattered from areas adjacent to the location of the potential anomaly, this is possible without having to re-scan the surface.

Another aspect of the invention is based on the recognition that while die-to-die comparison of areas on the same surface may be difficult when rotational motion is caused between the illumination beam and the surface inspected during inspection, it may still be possible to compare corresponding areas of two different surfaces that are inspected so that the performance of the surface inspection system can be much improved for inspecting surfaces with similar patterns thereon. The two surfaces may be scanned sequentially or simultaneously by a beam or beams of radiation. Radiation scattered from at least a portion of the first surface is collected and radiation scattered from at least a portion of the second surface is also collected. Preferably the two portions of the two surfaces have substantially the same relative locations on the first and second surfaces and substantially the same relative orientation with respect to the beam or beams and the collection optics collecting radiation scattered from the two respective areas. The radiation collected from the portions of the two surfaces or signals derived therefrom are used to determine or confirm the presence of potential anomalies in or on the portions of the first and/or the second surface.

BRIEF DESCRIPTION OF THE DRAWINGS

FIG. 7 shows partially in perspective and partially in block diagram form a system for inspecting anomalies of a semiconductor wafer surface, where two dimensional translational motion is caused between a radiation beam and the inspected surface, useful for illustrating the invention.

FIG. 11 is a collection of 32 different views of radiation in different directions from the same area of a surface that is inspected having a pattern thereon.

For simplicity in description, identical components are labeled by the same numerals in this application.

DETAILED DESCRIPTION OF THE EMBODIMENTS

The description below in reference to FIGS. 1 through 6B is similar to the description of similar figures in U.S. Pat. No. 6,538,730, which is incorporated herein in its entirety by reference. The optical systems of the patent are useful for illustrating the invention.

Figure 1:
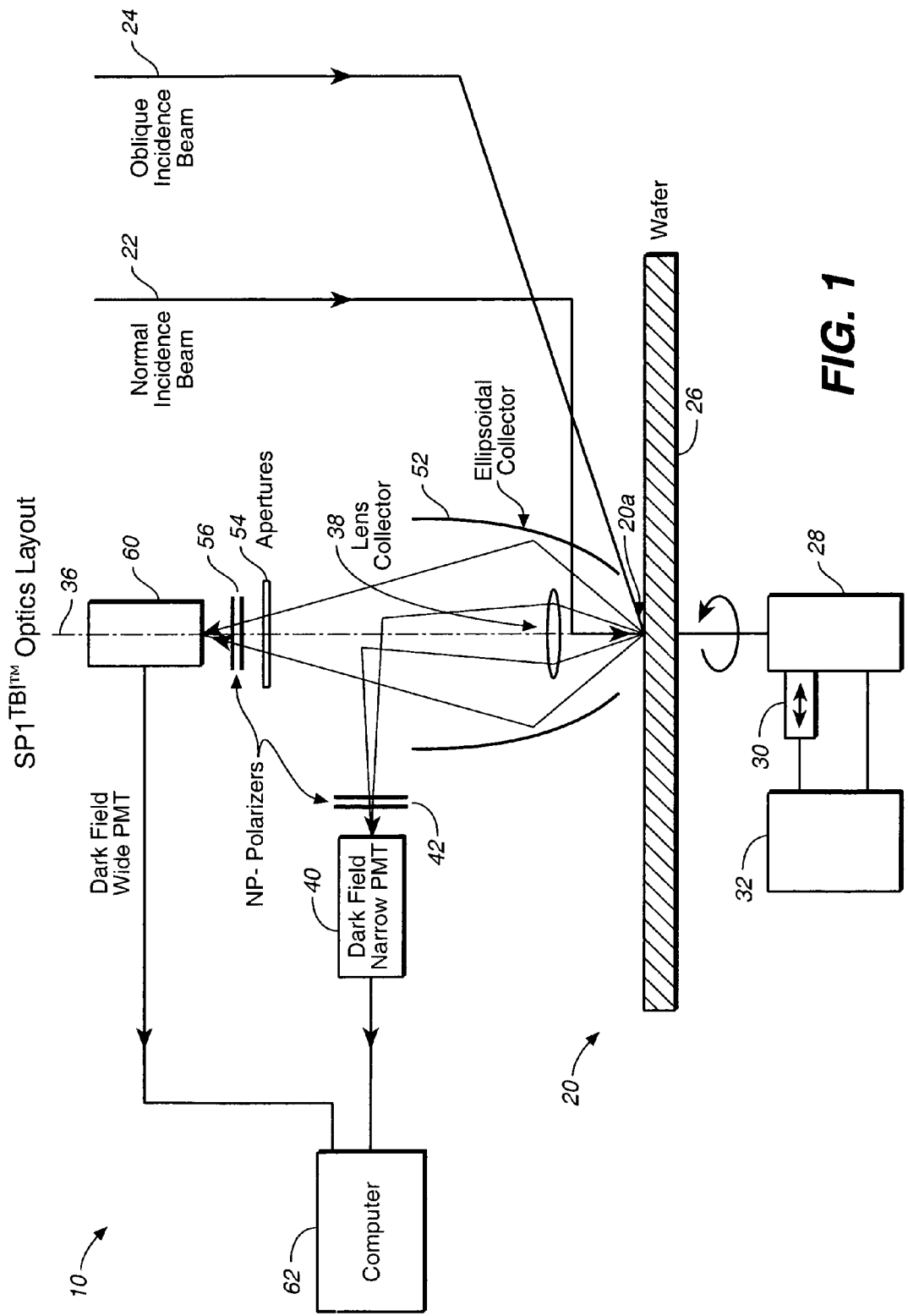
FIG. 1 is a schematic diagram of the SP1$^{TBI}$ system, where rotational and translational motion is caused between a radiation beam and the inspected surface, useful for illustrating the invention.

FIG. 1 is a schematic view of the SP1$^{TBI}$ system 10 available from KLA-Tencor Corporation of San Jose, Calif., the assignee of the present application. Aspects of the SP1$^{TBI}$ system 10 are described in U.S. Pat. Nos. 6,271,916 and 6,201,601, both of which are incorporated herein in their entireties by reference. To simplify the figure, some of the optical components of the system have been omitted, such as components directing the illumination beams to the wafer. The wafer 20 inspected is illuminated by a normal incidence beam 22 and/or an oblique incidence beam 24. Wafer 20 is supported on a chuck 26 which is rotated by means of a motor 28 and translated in a direction by gear 30 so that beams 22 and/or 24 illuminates an area or spot 20a which is caused to move and trace a spiral path on the surface of wafer 20 to inspect the surface of the wafer. Motor 28 and gear 30 are controlled by controller 32 in a manner known to those skilled in the art. Alternatively, the beam(s) 22, 24 may be caused to move in a manner known to those skilled in the art to trace the spiral path or another type of scan path.

The area or spot 20a illuminated by either one or both beams on wafer 20 scatters radiation from the beam(s). The radiation scattered by area 20a along directions close to a line 36 perpendicular to the surface of the wafer and passing through the area 20a is collected and focused by lens collector 38 and directed to a photomultiplier tube ("PMT") 40. Since lens 38 collects the scattered radiation along directions close to the normal direction, such collection channel is referred to herein as the narrow channel and PMT 40 as the dark field narrow PMT. When desired, one or more polarizers 42 may be placed in the path of the collected radiation in the narrow channel.

Radiation scattered by spot 20a of wafer 20, illuminated by either one or both beams 22, 24, along directions away from the normal direction 36 is collected by an ellipsoidal collector 52 and focused through an aperture 54 and optional polarizers 56 to dark field PMT 60. Since the ellipsoidal collector 52 collects scattered radiation along directions at wider angles from the normal direction 36 than lens 38, such collection channel is referred to as the wide channel. The outputs of detectors 40, 60 are supplied to a computer 62 for processing the signals and determining the presence of anomalies and their characteristics. In the conventional operation of the SP1$^{TBI}$ system, the intensities of the outputs of detectors 40, 60 are compared to threshold(s). When such detector output intensities exceed the threshold(s), the locations from which scattered radiation is detected by the detectors to provide such outputs then potentially have anomalies, and both the locations and the corresponding intensities of the detector outputs are stored.

Microview Without Re-Scan

As noted above, in the conventional operation of the SP1$^{TBI}$ system, both the detector output intensities as well as the locations from which scattered radiation is detected by the detector(s) to provide such output intensities are not stored unless such locations have been determined to contain potential anomalies, typically by comparing such intensities to a certain threshold. When surfaces with pattern or noisy background are inspected, there may be a large number of locations determined to have potential anomalies. In order to further examine the locations determined by conventional operation of the SP1$^{TBI}$ system to potentially have anomalies, it may be necessary to review all such locations at high resolution. Such operation, however, is time consuming so that it may be desirable to briefly review each of the locations in a microview mode before they are examined at high resolution. Such review normally requires knowledge of the intensities of the scattered radiation from areas surrounding the locations identified to have potential anomalies. During the conventional operation of the SP1$^{TBI}$ system, such information is not recorded so that during a conventional microview mode, the user would have to rescan such locations and the surrounding areas in order to record the scattered radiation from the surrounding areas as well as scattered radiation from the locations. This is cumbersome and time consuming.

One aspect of the invention is based on the recognition that, instead of recording only the detector output intensities that exceed certain thresholds, one would record and store the detector output intensities from portions of the surface in the vicinity of locations with potential anomalies where such intensities do not exceed the preset thresholds. In this manner, data indicating the scattered radiation intensities from portions of the wafer surface surrounding locations containing potential anomalies is available for review immediately after the inspection of the surface. The user can then quickly examine an area or patch of the wafer surface containing locations of potential anomalies for confirming whether such locations contain potential anomalies (and therefore merits detailed and/or high resolution examination) without having to re-scan the wafer surface. Thus, in reference to FIG. 1, in one embodiment, computer 62 stores in its associated memory (not separately shown) the detector output intensities provided by the detector or detectors in response to scattered radiation from all portions of the wafer, and not just the detector output intensities from locations where potential anomalies were identified.

To economize on the amount of memory that may be required for storage, it may be desirable to erase or discard the detector output intensities further away from locations containing potential anomalies. This is illustrated in reference to FIG. 9A.

Figure 9A:
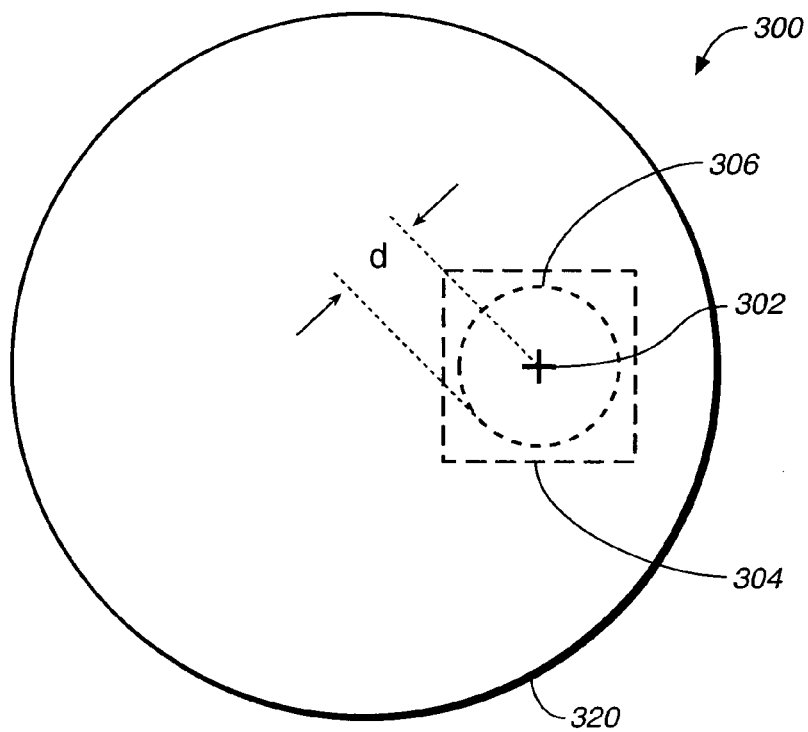
FIG. 9A is a schematic view of a surface that is inspected by a surface inspection system used for illustrating different aspects of the invention.

FIG. 9A is a schematic view of a semiconductor wafer surface where a potential anomaly has been determined to exist at location 302. To permit further review of the detector output intensity data at location 302 as well as the detector output in response to scattered radiation from areas surrounding location 302 for confirmation of the potential anomaly at the location, it may be adequate to store the detector outputs corresponding to radiation scattered from an designated area 304 containing location 302. Then the detector output intensities in response to scattered radiation from portions of the wafer surface 300 outside the area 304 may be discarded or erased if no location in the vicinity of such portions is identified to contain a potential anomaly. Thus if the surface 300 contains more than one location with potential anomalies, areas or patches similar to patch 304 may be designated where each of the areas or patches contains one of the locations and storage of the detector output intensities will be retained only for portions of surface 300 within such areas or patches so that the remaining data may be erased. For example, where the shape of the patch is circular (e.g. patch 306 in FIG. 9A) with radius d, and the detector output intensities are recorded in the form of pixels, the pixel data may be erased if no potential anomaly has been identified on the surface within distance d from such pixel. The area designated or distance d may be set prior to the inspection.

The capability of the surface inspection system to perform microview without re-scanning the surface is not limited to systems such as the SP1$^{TBI}$, where both locational and translational motion is caused between the illumination beam or beams and the surface inspected. Thus all of the above features of recording detector output intensities for either the entire wafer or those corresponding to patches may be applicable to systems where two dimensional translational motion is caused between the illumination beam or beams and the surface inspected as described in more detail below.

The above-described microview without requiring re-scan capability can be further enhanced where scattered radiation from the surface that is being inspected is collected and detected at a different number of directions at different azimuthal and/or elevation angles, in a scheme known as acquiring a multi-perspective view of the surface as described below.

Figure 10A:
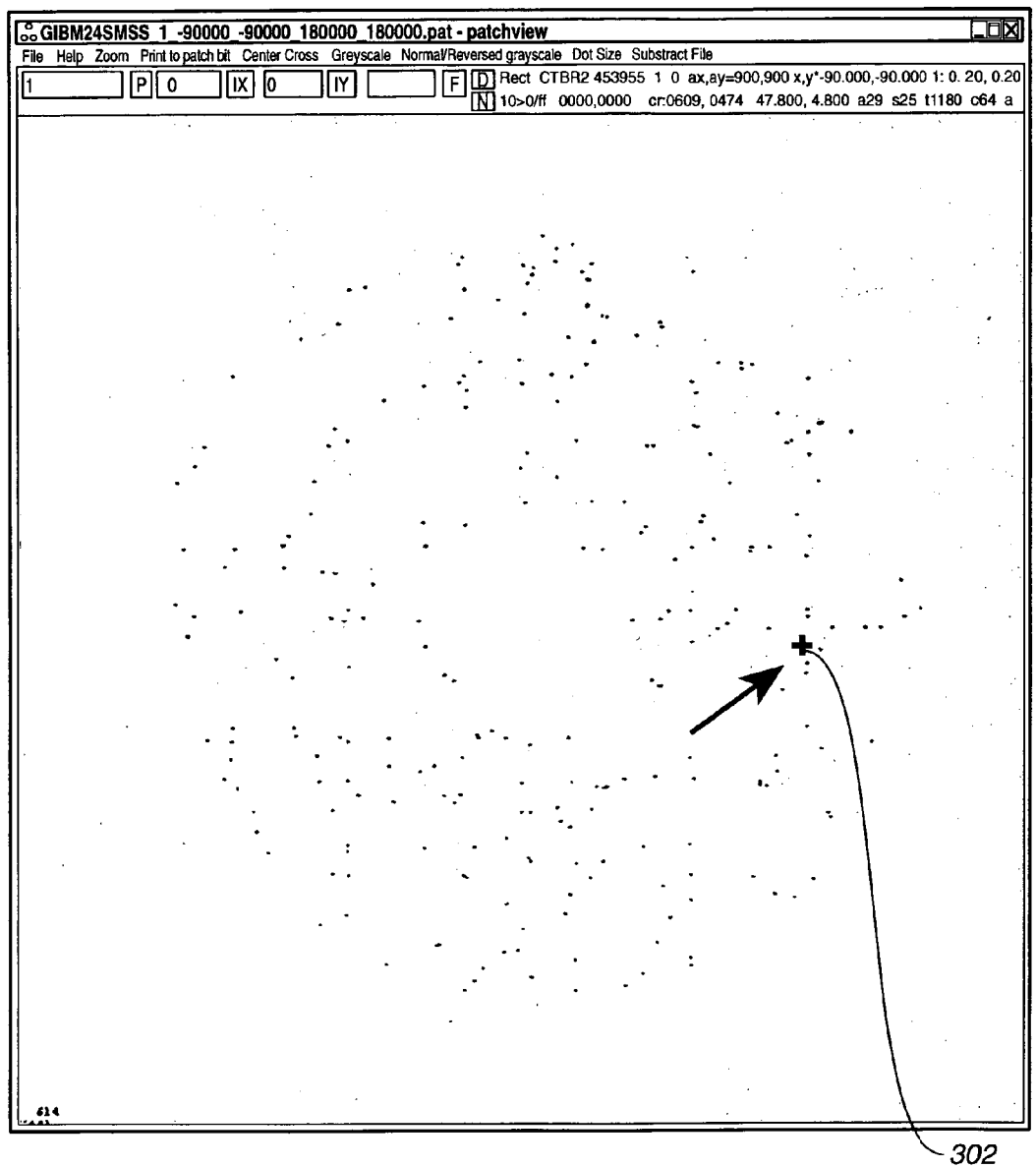
FIG. 10A is a schematic view of a defect map of a semiconductor wafer with logic circuits thereon to illustrate the invention.

The microview without re-scan feature is illustrated in FIGS. 10A-10D. FIG. 10A is a schematic view of a defect map of a semiconductor wafer with logic circuits thereon provided in a conventional microview mode requiring re-scan. A defect map is constructed by identifying the pixel intensities of the detector outputs with the pixel locations of the surface from which scattered radiation is detected to provide such intensities, and such map can be displayed as shown in FIG. 10A. As described above, the detector intensity outputs are stored in the conventional microview mode only when such intensities fall above a predetermined threshold. Thus, to obtain a defect map, computer 62 compares detector intensities on the surface to a predetermined threshold or thresholds and identify the locations on the surface 20 where intensity of scattered radiation exceeds the threshold or thresholds. Such locations together with their associated detected pixel intensities are then reported to form the defect map shown in FIG. 10A. The potential defects are shown as dots on the map, such as dot 302.

Figure 10B:
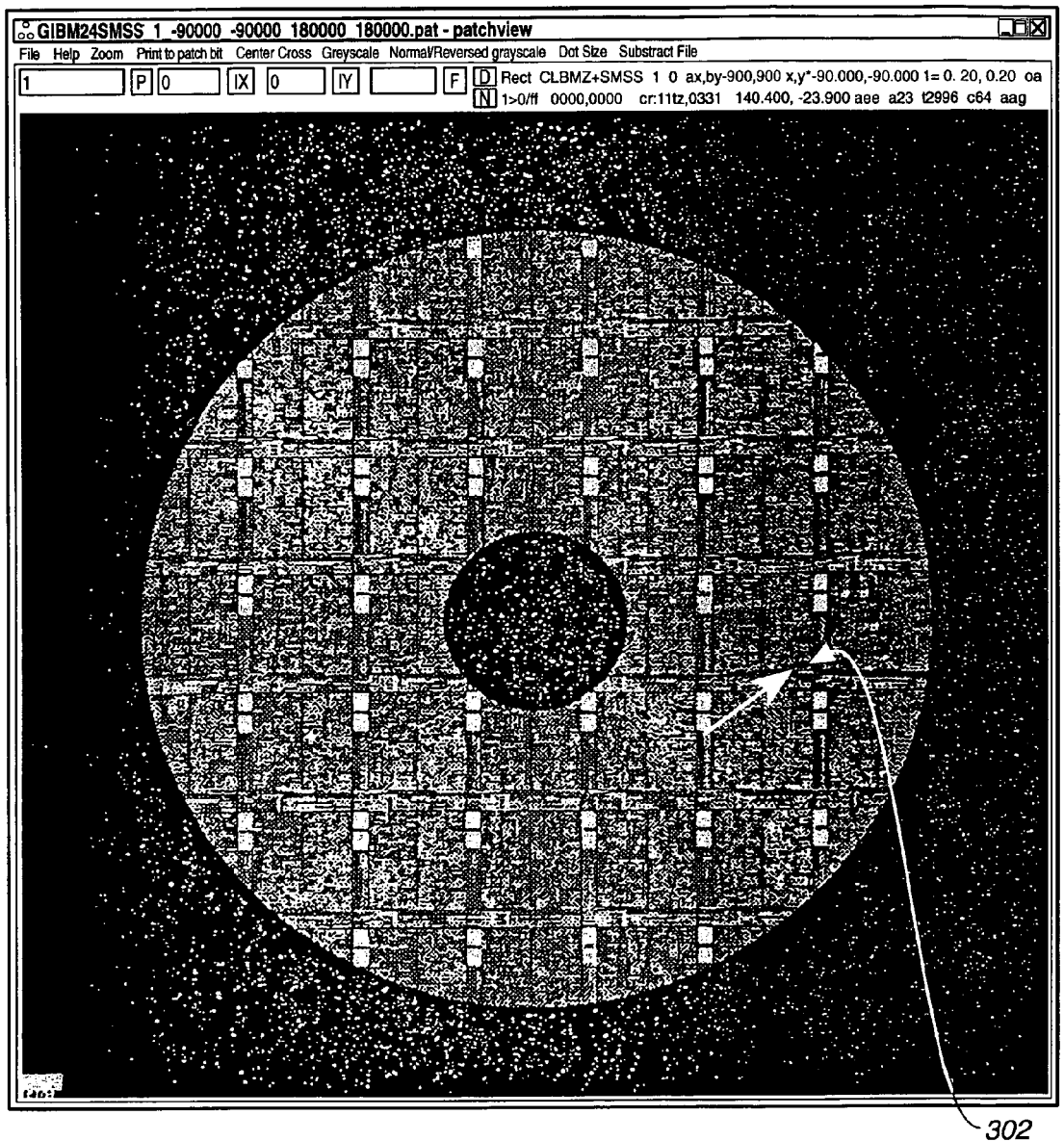
FIG. 10B is an intensity map of the semiconductor wafer of FIG. 10A, where radiation scattered from areas surrounding the defects are shown in addition to the defects themselves to illustrate the invention.

FIG. 10B illustrates a map of the semiconductor wafer whose defect map is shown in FIG. 10A. FIG. 10B is obtained using the improved technique described above where re-scan of the wafer is unnecessary. FIG. 10B illustrates detector the output intensities of scattered radiation detected from the entire wafer of FIG. 10A, where the detector output intensities are shown not only for locations with potential anomalies, but intensities for all locations on the wafer.

Figure 10C:
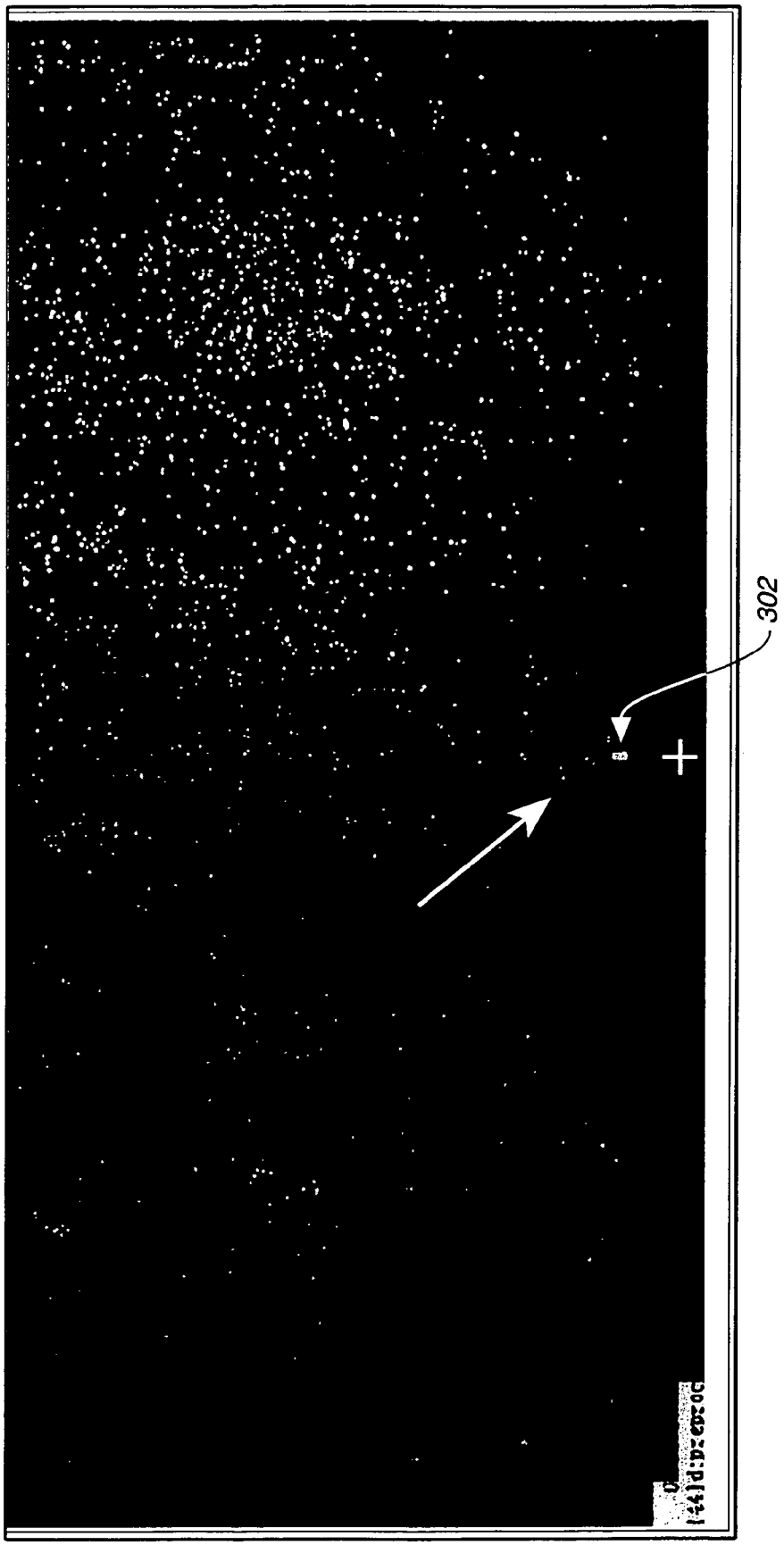
FIGS. 10C and 10D are views of patches on the semiconductor wafer of FIGS. 10A and 10.

For the purpose of recording and storing the detector output intensities for the construction of maps such as those shown in FIGS. 10A and 10B, the surface of the wafer is divided into pixels and an output intensity value is associated with each pixel. The maps of FIGS. 10A and 10B are then constructed using such pixel intensity values. The location 302 of a potential anomaly of FIG. 9A is also shown in FIGS. 10A and 10B. FIG. 10C is a view of an area or patch of the defect map of FIG. 10A where the patch or area contains the location 302. Unlike the defect map of FIG. 10A, however, the patch view in FIG. 10C shows the defect 302 as a white dot on a dark background.

Figure 10D:
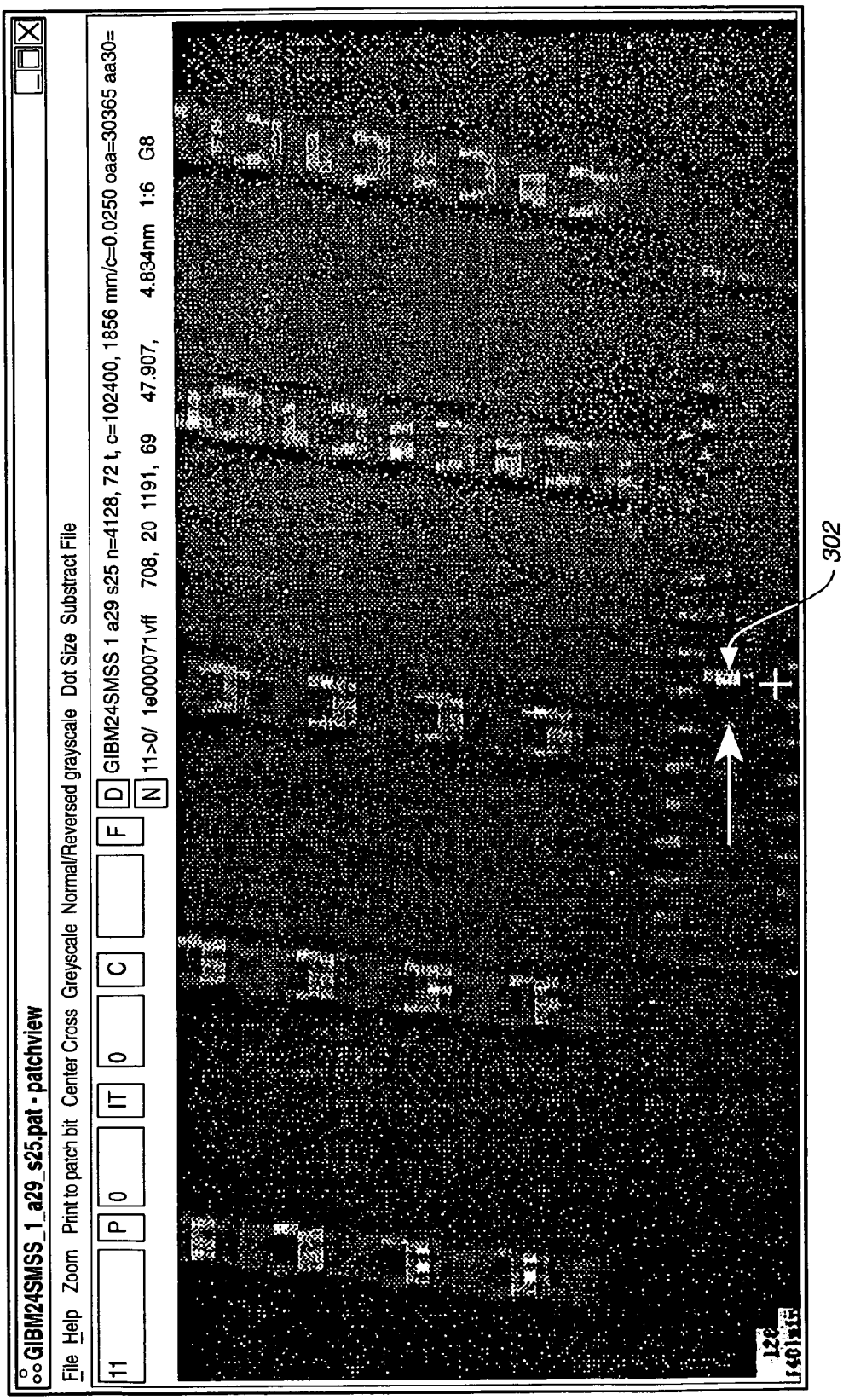

According to an embodiment of one aspect of this invention, when the user wishes to also observe the pixel intensities in an area of patch of the wafer map containing the defect 302, all the user would have to do is to double click the computer mouse (not shown) at location 302 on a computer screen displaying the map in FIG. 10A, and computer 62 would present a view showing all the pixel intensities within the patch or area of the wafer in FIG. 10A, as shown in FIG. 10D. As noted above, since computer 62 has stored in its memory either all the pixel intensities of the entire surface 20, or at least the pixel intensities in areas or patches containing the locations of potential anomalies, all of the pixel intensities shown in FIG. 10D would be stored in the memory of computer 62, so that the re-scanning of the surface 20 would be unnecessary in the improved microview mode. Thus as can be seen from FIG. 10D, viewing the potential defect at location 302 in the context of its surroundings makes it easier for the user to determine whether an anomaly indeed exists at location 302. If the user determines that a potential anomaly indeed exists at location 302, then this portion of the surface can be further examined at higher resolution or with even more elaborate measures to examine this location and its surroundings for determination and classification of the anomaly. By avoiding the necessity to re-scan the wafer, however, this process of identifying and reviewing potential anomalies is much faster and less cumbersome than conventional microview.

Rotational Symmetry

The SP1$^{TBI}$ system is advantageous for unpatterned wafer inspection since the collection optics (lens 38 and mirror 52) is rotationally symmetric about the normal direction 36, so that the orientation of the system in FIG. 1 relative to the orientation of defects on the surface of wafer 20 is immaterial. In addition, the angular coverage of the scattering space by these collectors is well matched to those required to detect the anomalies of interest in unpatterned wafer inspection applications.

In addition to the above characteristic, however, the SP1$^{TBI}$ system 10 has another important characteristic in that both its lens collector 38 and the ellipsoidal mirror collector 52 preserve the azimuthal information contained in radiation scattered by defects on surface of wafer 20. Thus, certain defects and/or pattern on the wafer may scatter radiation preferentially along certain azimuthal directions more than other azimuthal directions. By making use of the preserved azimuthal information in the collected radiation by the collectors 38 and 52, system 10 may be advantageously adapted and modified for the detection of defects on patterned wafers.

By segmenting the radiation collected by the lens 38 and/or ellipsoidal mirror 52, radiation scattered in different azimuthal directions may be detected separately. In this manner, the detectors detecting radiation diffracted or scattered by pattern may become saturated, while other detectors not detecting such diffraction or scatter will yield useful signals for the detection and classification of defects on wafer 20. Since the lens 38 and ellipsoidal mirror 52 preserve the azimuthal information of the scattered radiation, knowledge of the type of pattern or defects present on wafer 20 can be advantageously used to design and position multiple detectors to advantageously detect and classify the defects on the wafer. This is especially true in the case of regular patterns such as memory structures on wafer 20, as will be explained below, since radiation diffracted by such regular patterns also tend to be regular.

Figure 2:
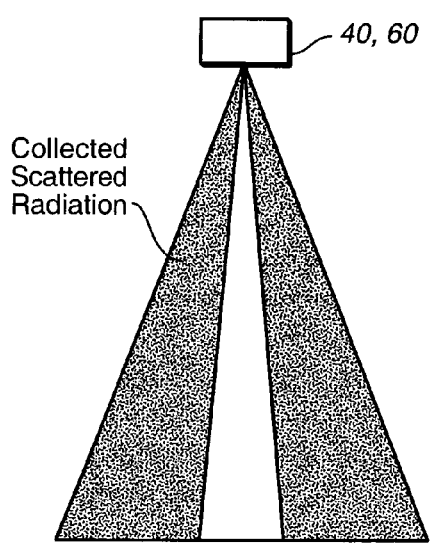
FIG. 2 is a schematic diagram illustrating a convergent hollow cone of radiation useful for illustrating the invention.

FIG. 2 is a schematic view illustrating a convergent hollow cone of radiation which can be collected by lens 38 or mirror 52. In the case of lens 38 of FIG. 1, a spatial filter (not shown in FIG. 1) is employed to block the specular reflection of the normal incidence beam 22 from reaching detector 40, so that the radiation focused by lens 38 to PMT 40 has the shape of a convergent hollow cone illustrated in FIG. 2. In the case of the ellipsoidal mirror 52, since the mirror is not a complete ellipse, it collects only radiation scattered at larger angles to the normal direction 36 without also collecting the radiation scattered at near normal directions, so that the radiation focused by mirror 52 towards detector 60 also has the shape of a convergent hollow cone as shown in FIG. 2.

Figure 3A:
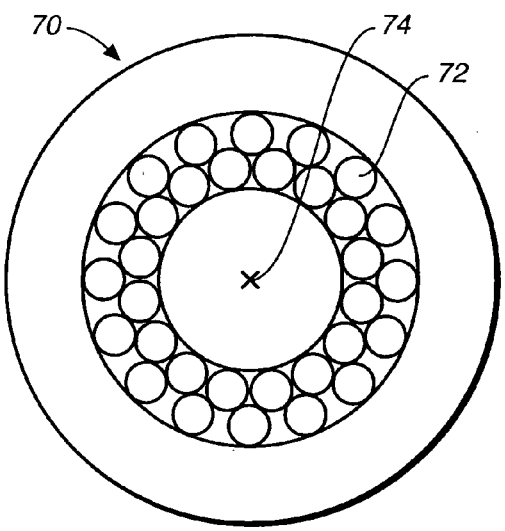
FIG. 3A is a schematic view of a possible arrangement of multiple fiber channels for carrying scattered radiation collected by the ellipsoidal collector of the system of FIG. 1 useful for illustrating the invention.

FIG. 3A is a schematic view of a possible arrangement of multiple fiber channels receiving radiation in the convergent cone of radiation shown in FIG. 2, such as that collected by mirror 52, to illustrate the preferred embodiment of the invention. The arrangement in FIG. 3A comprises two substantially concentric rings of optical fiber channels 72 that are used to carry the collected scattered radiation in the convergent hollow cone shown in FIG. 2. Fourier components or other pattern scattering from the pattern on the wafer 20 may reach some of the fibers 72, thereby causing the detectors detecting the radiation from such channels to be saturated or provide large amplitude signals. However, there will be other optical fiber channels that do not receive such unwanted pattern scattering. The use of multiple fiber channels 72 effectively segments the collected scattered radiation into different sectors or segments so that only some of the fiber channels will receive a strong signal and can become saturated or provide high amplitude outputs due to the Fourier or other pattern scatter leaving the remaining channels carrying information that can be analyzed for detecting anomalies. As will be explained below, since the azimuthal information in the collected scattered radiation in the cone of FIG. 2 is preserved, various schemes may be employed to minimize the effects of the pattern scatter when the segmented approach of FIG. 3A is used.

Figure 3B:
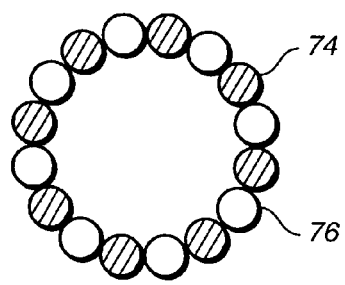
FIG. 3B is a schematic view of an multi-anode photomultiplier tube (PMT) that can be used in conjunction with an arrangement of multiple fiber channels such as that shown in FIG. 3A useful for illustrating the invention.

Different types of detectors may be used to detect the radiation carried by the fiber channels 72, such as the multi-anode PMT shown in FIG. 3B. In the event a multi-anode PMT is used, however, there is a nominal three percent cross-talk between any two adjacent channels. To avoid such cross-talk, fibers 72 may be aligned with every other PMT anode, in a manner illustrated in FIG. 3B. FIG. 3B is a schematic view of a multi-anode PMT. As shown in FIG. 3B, only the anodes 74 that are shaded are aligned with fibers 72, where anodes 76 are not aligned with any of the fibers 72. This avoids the three percent cross-talk that may be present if all of the anodes shown in FIG. 3B are aligned with fibers 72.

Figure 4:
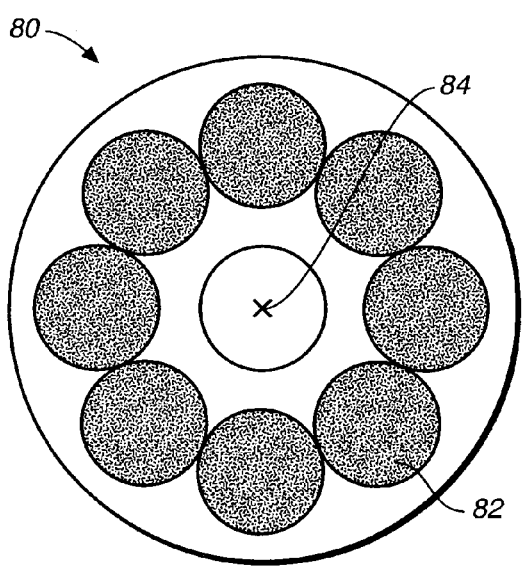
FIG. 4 is a schematic view of an arrangement of fiber channels/multiple detectors for carrying scattered radiation collected by the lens collector in the narrow channel of the system of FIG. 1 useful for illustrating the invention.

FIG. 4 is a schematic view illustrating an arrangement 80 of fiber channels or multiple detectors 82 for the narrow channel. Thus, fibers or detectors 82 may be aligned with the collected scattered radiation illustrated in FIG. 2 for the narrow channel collected by lens 38 for segmenting the radiation in a similar manner as that described above for the wide channel.

Figure 5A:
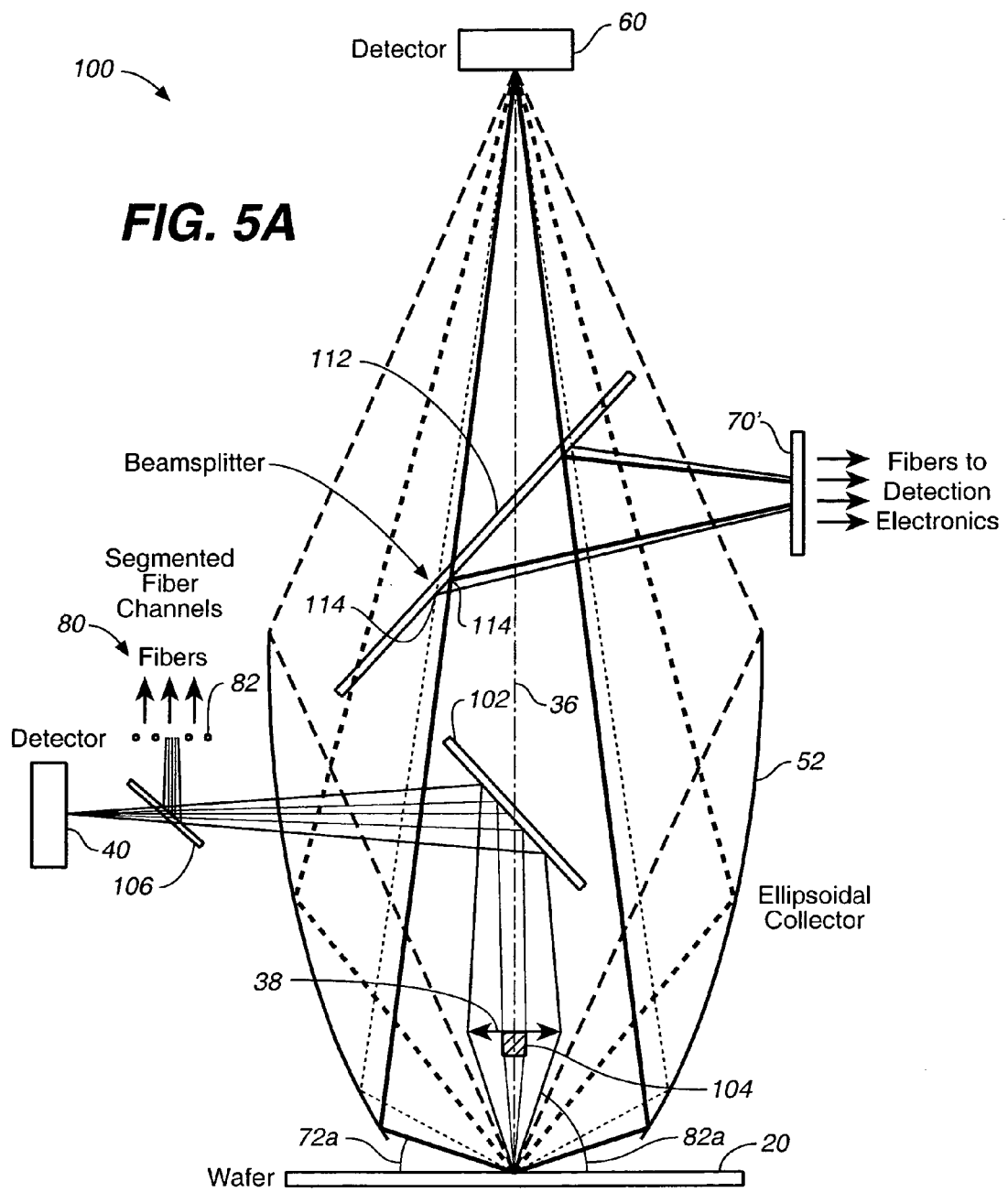
FIG. 5A is a cross-sectional view of a defect inspection system useful for illustrating the invention.

FIG. 5A is a partially cross-sectional view and partially schematic view of a defect inspection system to illustrate the preferred embodiment of the invention. To simplify FIG. 5A, the two illumination beams 22 and 24, computer 62 and the mechanisms for moving the wafer are not shown in the figure. Radiation scattered by spot 20a on wafer 20 and collected by lens 38 is reflected by mirror 102 to detector 40. Stop 104 blocks the specular reflection of the normal incident beam 22 from detector 40 and results in a cone shape of the convergent beam in FIG. 2. The beam collected and focused by lens 38 and reflected by mirror 102 passes through a beam splitter 106 and a portion of the collected radiation that passes through the beamsplitter is focused onto detector 40 to provide a single output as would be the case in normal SP1$^{TBI}$ operation. Beamsplitter 106 reflects and diverts a portion of the collected radiation from lens 38 to the arrangement 80 of optical fibers of FIG. 4. Preferably, the size of optical fibers 82 and the size of the hollow cone reflected by beamsplitter 106 are such that fibers 82 collect and convey most of the radiation in the hollow cone of radiation. Each of the fibers 82 is then connected to a corresponding detector or a detecting unit in a multi-unit or multi-element detector. In a similar manner, beamsplitter 112 diverts a small portion of the radiation collected by ellipsoidal mirror 52 towards arrangement 70' of optical fiber channels 72, shown more clearly in FIG. 5B (or FIG. 3A), where each channel 72 is connected to a separate detector or a separate detecting unit in a multi-element detector system (not shown). As shown in FIG. 5A, beamsplitter 112 is such that it diverts radiation only within a narrow ring 114 to arrangement 70'. Most of the radiation collected by mirror 52 is passed through beamsplitter 112 and focused to detector 60 to provide a single output as would be the case in normal SP1$^{TBI}$ operation. In FIG. 5A, the illumination beams 22, 24 and the mechanisms for moving the wafer have been omitted to simplify the figure.

As will be evident from a comparison of system 10 of FIG. 1 and system 100 of FIG. 5A, system 100 retains substantially all of the features of system 10 of FIG. 1. In addition, system 100 diverts a portion of the scattered radiation collected by each of lens 38 and mirror 52, and directs it towards fibers 82, 72 to convey the segmented radiation to separate detectors or detecting units. The system is compact and requires minimal additional space compared to the SP1$^{TBI}$ system 10 of FIG. 1. In this manner, a single combined instrument may be optimized and used for both unpatterned and patterned wafer inspection, thereby eliminating the need for two separate instruments for the two types of wafer inspection.

Figure 6A:
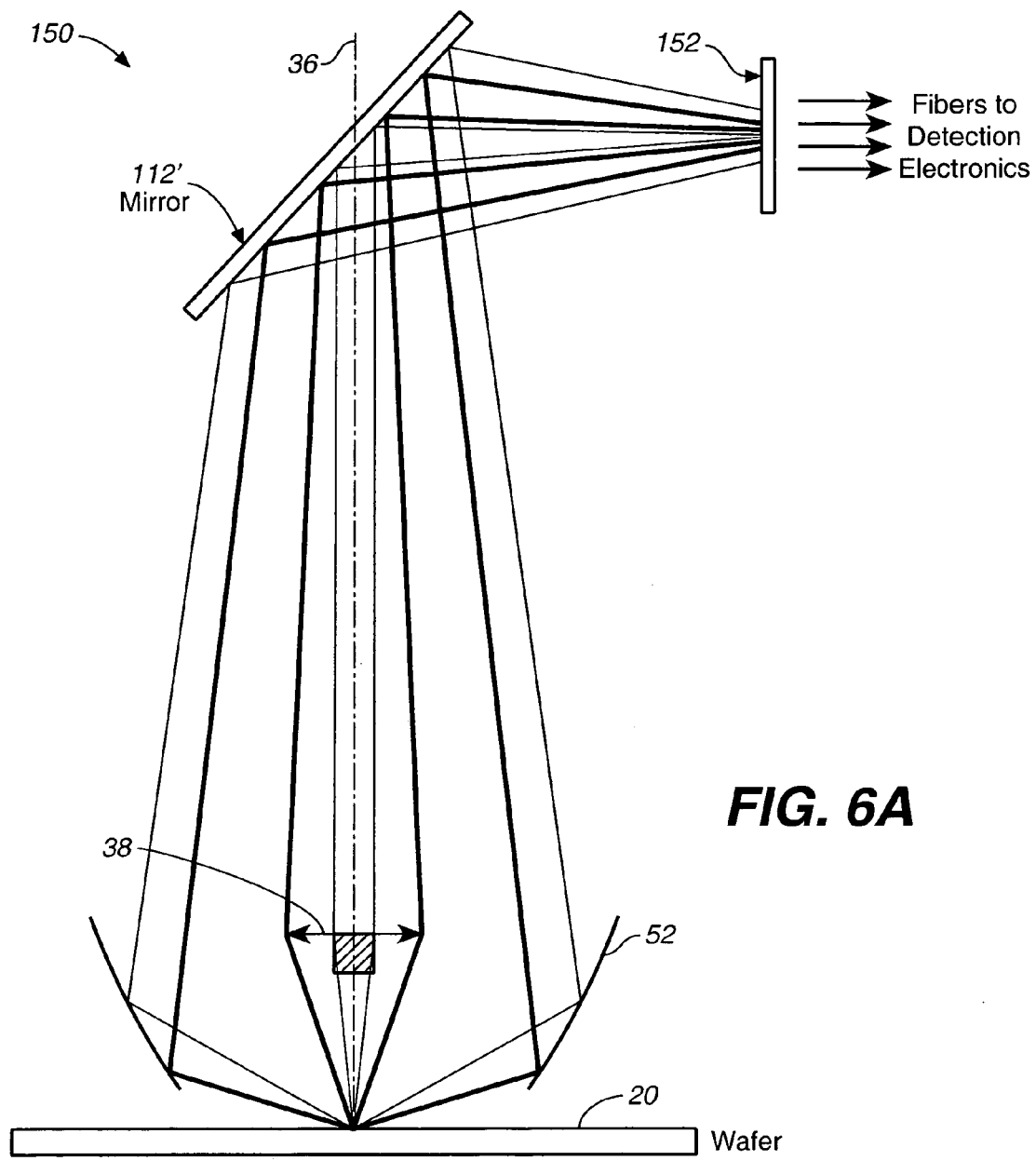
FIG. 6A is a cross-sectional view of an alternative defect inspection system useful for illustrating the invention.
Figure 6B:
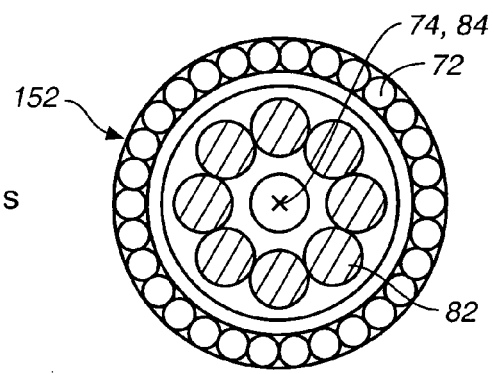
FIG. 6B is a cross-sectional view of an arrangement of segmented optical channels used in the embodiment of FIG. 6A.

When only patterned wafers are to be inspected, an alternative defect inspection system 150 of FIG. 6A may be used. In FIG. 6A, the illumination beams 22, 24, computer 62 and the mechanisms for moving the wafer have been omitted to simplify the figure. As shown in FIG. 6A, scattered radiation collected by lens 38 and by mirror 52 are reflected by mirror 112' towards an arrangement of optical fibers 152 which is shown more clearly in cross-section in FIG. 6B. As shown in FIG. 6B, arrangement 152 includes a ring of fibers 82 conveying scattered radiation collected by lens 38 and a ring of fibers 72 conveying scattered radiation collected by mirror 52. As before, each of the fibers 72, 82 may be connected to a separate detector or a detecting unit of a multi-unit detector.

Figure 5B:
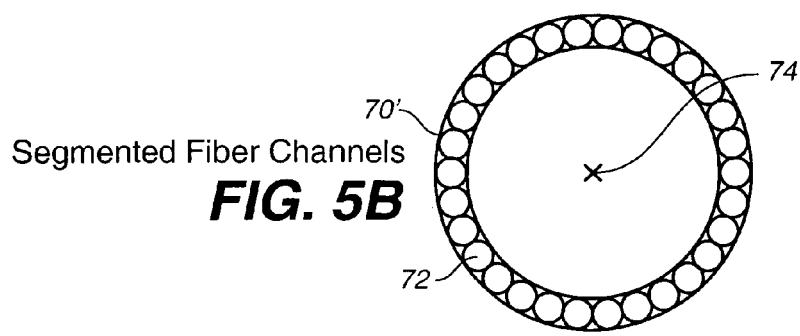
FIG. 5B is a cross-sectional view of an arrangement of separate optical channels used in the embodiment of FIG. 5A.

While a single ring of detectors are shown in FIGS. 4 and 5B, multiple rings may be employed such as that shown in FIG. 3A. The optically transmissive cores of optical fibers that are located adjacent to each other in each of the two arrangements 70, 70', 80 are separated from each other by the claddings that envelope the cores so that crosstalk between adjacent cores is reduced. Obviously, optical channels other than fibers may be used and are within the scope of this invention. Where such channels do not include separators such as the cladding in the case of optical fibers, other optical separators may be employed to reduce crosstalk.

Systems 100 and 150 of FIGS. 5A and 6A are particularly advantageous for distinguishing between micro-scratches and particles. The scattering pattern due to a micro-scratch gives the highest concentration of energy and greatest detection uniformity when illuminated normally and captured in the near normal or narrow channel collected by lens 38. The unique signature of the scratch in the form of an elongated pattern in the far-field, allows for a simple method of classification. Therefore, if the eight or more fibers 82 arranged in a ring format is placed in the path of the hollow cone of light focused by lens 38 towards fibers 82 as diverted by beamsplitter 106, where the outputs of these fibers are directed onto a multi-channel detector or an array of individual detectors, by a simple process of comparing the signals obtained through any two diagonally opposed fibers relative to the signals in the remaining fibers, the presence of the micro-scratch is obtained. When illuminated obliquely, micro-scratches result in scattering patterns which can be distinguished from those due to particles, by using the multiple detection channels that were described above in conjunction with pattern inspection, viz. multiple fiber units 70 and 70'. In both the wide and narrow channels, it is also possible to place individual detectors or multi-element detecting systems directly in the path of the converging hollow cone of light, rather than individual optical fibers.

In the manner described above, the collection space for scattered radiation from the surface may be segmented in the azimuthal directions. In a similar manner, the collection space for scattered radiation from the surface may be segmented in the elevation directions as well, which are defined by the elevation angles of such directions relative to the surface inspected. For example, the elevation collection angles of fibers 82 (e.g. 82a in FIG. 5A) are different from those of fibers 72 (e.g. 72a in FIG. 5A), and elevation collection angles of the inner ring of fibers 72 in FIG. 3A are different from those of fibers 72 in the outer ring.

Multiperspective Applied to Surfaces with Pattern

Where systems 100, 150 are used for inspecting wafers with memory cells thereon, the Fourier components in the radiation scattered by the memory array will spin as the wafer is rotated. These components will thus rotate and be at different azimuthal angles about the normal direction 36 of FIGS. 1, 5A and 6A. This means that these Fourier components will be conveyed by different fibers 72, 82 as the wafer is rotated. Since the array of memory cells may have different dimensions in the X and Y directions of the wafer, as the wafer rotates, the number of detectors that are saturated by the Fourier components may change. This can be provided for by knowing the X and Y dimensions of the memory cells so that the number of Fourier diffraction components can be estimated. Alternatively, during an initialization process at the beginning, a learn cycle is performed where the maximum number of Fourier components that need to be eliminated is determined by noting the maximum number of detectors with very strong, or saturated, outputs. During the subsequent measurement after initialization, this number of detector outputs may then be eliminated, where the outputs eliminated are the ones that are saturated or the ones that have the largest values. In the case of a multi-anode PMT, for example, where each anode is used and is connected to a corresponding fiber, cross-talk may be reduced by also eliminating the components adjacent to the detectors having the highest outputs. For example, if the wafer in one position gives three Fourier components, and in another two, the three direct components together with two components adjacent to each would be eliminated for a total of nine detector outputs that are eliminated. This leaves seven useable detector outputs. This number will be maintained regardless of the exact orientation of the wafer. This allows the user to maintain the sizing option for the particles.

Preferably the fibers 72 and 82 are arranged rotationally symmetrically around a direction, such as axes 74 and 84 shown in FIGS. 3A, 4, 5B and 6B. When arranged in such manner, the radiation scattering directions are partitioned into identical angular segments and radiation scattered within each segment is collected by a corresponding fiber. When beamsplitter or mirror 102, 112, 112' reflects or diverts a portion of the radiation collected by lens 38 or mirror 52, the azimuthal positions of the collected scattered radiation is preserved when the reflected or diverted radiation is directed to the fibers 72, 82. When such radiation is so reflected or diverted, axes 74, 84 correspond to the normal direction 36, and the azimuthal positions of the collected scattered radiation about the axes 74, 84 corresponding to their azimuthal positions about the normal direction 36 are preserved. It is also possible to collect scattered radiation at different elevation angles (i.e. at different angles from the surface inspected). For example, fibers 72 collect radiation scattered at elevation angles different from those at which scattered radiation is collected by fibers 82. This provides multiperspective views of the scattered radiation originating from the illumination beam(s) from the inspected surface.

Microview and Multiperspective

Figure 11:
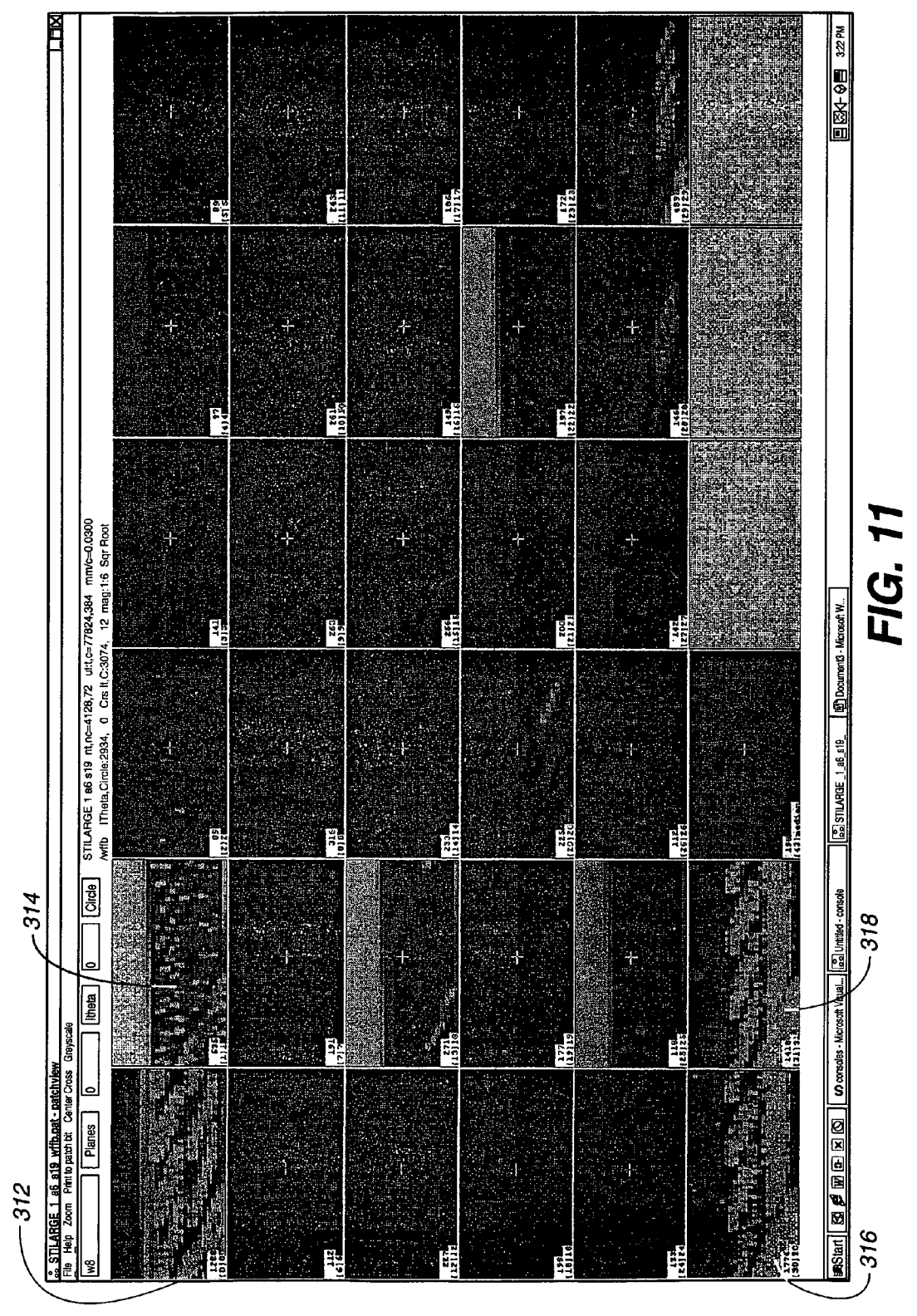

The above described features providing multiperspective views (i.e. portions of maps) of the scattered radiation from the inspected surface can be combined with the above described microview capability. For example, any one of the systems 10, 100 and 150 of FIGS. 1, 5A and 6A may be used to scan the surface 20, and the intensities of the detector outputs are stored (such as in memory associated with computer 62), whether or not such intensities exceed predetermined thresholds. Upon completion of the scan, it is possible for a user to obtain a microview of an area or patch containing the location of interest (such as location 302 in FIG. 10A) at different elevation and/or azimuthal angles. This is illustrated, for example, in FIG. 11. FIG. 11 is a collection of 32 views (microviews) of the same patch or area of the inspected surface obtained by detecting intensities of radiations scattered by the patch into 32 different directions. Thus, the 32 directions may differ from one another by azimuthal angle, elevation angle from the inspected surface, or both. As can be observed from FIG. 11, the pixel intensity values in some of the views of the patches (312, 314, 316 and 318) contain high intensity scattered radiation. This may indicate that the views 312-318 contained scattered radiation from pattern or other periodic irregularities of surface 20. For this reason, these four views may be ignored in the determination of the existence of anomalies on the surface 20. As noted above, different types of defects or anomalies will scatter radiation at different preferential elevation or azimuthal angles. By providing a large number of views from different collection angles (both azimuthal and elevation), much more information is available for determining both the presence and the type of anomalies that may be present on surface 20.

In reference to FIG. 11, where the surface inspected contains pattern or other noisy background, the various collection channels at different collection angles will show different perspectives of the same patch or area on the inspected surface. Patterns such as memory arrays on the surface cause strong scattering in particular preferential directions. To reduce the affect of pattern scattering on anomaly detection, it may be desirable to discard detector outputs that are saturated or where the pixel intensity is too high to be caused by scattering from anomalies. Thus one may discard all together the views 312-318. Of the remaining views, it may be desirable to provide a suitable value for each pixel in the area or patch, such as by computing a weighted average of the pixel intensities from the different multiperspective views of the same area or patch. In one embodiment, this value may also be a median value. Alternatively, the minimum value among the remaining views may be selected instead. Thus a view of an area or patch of the inspected surface may be formed by the weighted average, median or the minimum pixel intensities of all the views that remain after discarding the ones that are saturated or having pixel intensities that are too high.

While it is possible for the systems described above to store and provide a large number of views of the entire surface inspected in multi-perspective, the amount of memory required can be substantial and too costly for certain applications. This may be the case even where pixel intensities are stored only for patches or areas containing locations of potential anomalies while discarding or erasing pixel intensities that are further away from such locations. Thus for some applications, it may be desirable to first scan the surface using only a single or a small number of collection channels and corresponding detectors, such as system 10 of FIG. 1. After a defect map such as that shown in FIG. 10A has been compiled using the results of the scan, the patches or areas containing locations of potential defects may be re-scanned with a larger number of collection channels and corresponding detectors than the number used during the previous scan, such as in the systems illustrated in FIGS. 2-6B, so that a larger number of different perspective views of these patches at different collection angles can be obtained. This process may be advantageous for certain applications.

Microview Using Different Inspection System

Another type of surface inspection system will now be described in reference to FIGS. 7 and 8. The description of this type of system is set forth in more detail in U.S. Pat. Nos. 6,215,551 and 5,864,394, which are herein incorporated by reference in their entireties. As shown in FIG. 7, system 220 includes a laser 222 providing a laser beam 224. Beam 224 is expanded by beam expander 226 and the expanded beam 228 is deflected by acousto-optic deflector (AOD) 230 into a defected beam 232. The deflected beam 232 is passed through post-AOD and polarization selection optics 234 and the resulting beam is focused by telecentric scan lens 236 onto a spot 210 on surface 240 to be inspected, such as that of a semiconductor wafer, photomask or ceramic tile, patterned or unpatterned.

In order to move the illuminated area 210 on surface 240 for scanning the entire surface, the AOD 230 causes the deflected beam 232 to change in direction, thereby causing the illuminated spot 210 on surface 240 to be scanned along a scan line 250. As shown in FIG. 7, scan line 250 is preferably a straight line having a length which is smaller than the dimension of surface 240 along the same direction as the scan line. Even where line 250 is curved, its span is less than the dimension of surface 240 along the same general direction. After the illuminated spot has completed scanning surface 240 along scan line 250, surface 240 of the wafer is moved by means of stage 244 (see FIG. 8) along the X axis so that the illuminated area of the surface moves along arrow 252 and AOD 230 causes the illuminated spot to scan along a scan line parallel to scan line 250 and in adjacent position spaced apart from scan line 250 along the negative X axis. After the illuminated spot has covered such scan line, surface 240 is moved by a small distance by means of stage 244 so that the area of the surface to be illuminated is moved along direction 252 in order to scan an adjacent scan line at a different X position. This small distance preferably is equal to about one quarter of the height of spot 210. This process is repeated until the illuminated spot has covered strip 254; at this point in time the illuminated area is at or close to the edge 254a. At such point, the surface 240 is moved along the Y direction by about the length of scan line 250 by means of stage 244 in order to scan and cover an adjacent strip 256, beginning at a position at or close to edge 256a. The surface in strip 256 is then covered by short scan lines such as 250 in a similar manner until the other end or edge 256b of strip 256 is reached at which point surface 240 is again moved along the Y direction for scanning strip 258. This process is repeated prior to the scanning of strip 254, 256, 258 and continues after the scanning of such strips until the entire surface 240 is scanned. Surface 240 is therefore scanned by scanning a plurality of arrays of short path segments the totality of which would cover substantially the entire surface 240.

The deflection of beam 232 by AOD 230 is controlled by chirp generator 280 which generates a chirp signal. The chirp signal is amplified by amplifier 282 and applied to the transducer portion of AOD 230 for generating sound waves to cause deflection of beam 232 in a manner known to those skilled in the art. For a detailed description of the operation of the AOD, see "Acoustooptic Scanners and Modulators," by Milton Gottlieb in Optical Scanning, ed. by Gerald F. Marshall, Dekker 1991, pp. 615-685. Briefly, the sound waves generated by the transducer portion of AOD 230 modulates the optical refractive index of an acoustooptic crystal in a periodic fashion thereby leading to deflection of beam 232. Chirp generator 280 generates appropriate signals so that after being focused by lens 236, the deflection of beam 232 causes the focused beam to scan along a scan line such as line 250 in the manner described.

Chirp generator 280 is controlled by timing electronic circuit 284 which in the preferred embodiment includes a microprocessor. The microprocessor supplies the beginning and end frequencies f1, f2 to the chirp generator 280 for generating appropriate chirp signals to cause the deflection of beam 232 within a predetermined range of deflection angles determined by the frequencies f1, f2. The auto-position sensor (APS) optics 290 and APS electronics 292 are used to detect the level or height of surface 240. Detectors such as detector 211b collects light scattered by anomalies as well as the surface and other structures thereon along scan line 250 and provides output signals to a processor in order to detect and analyze the characteristics of the anomalies.

Figure 8:
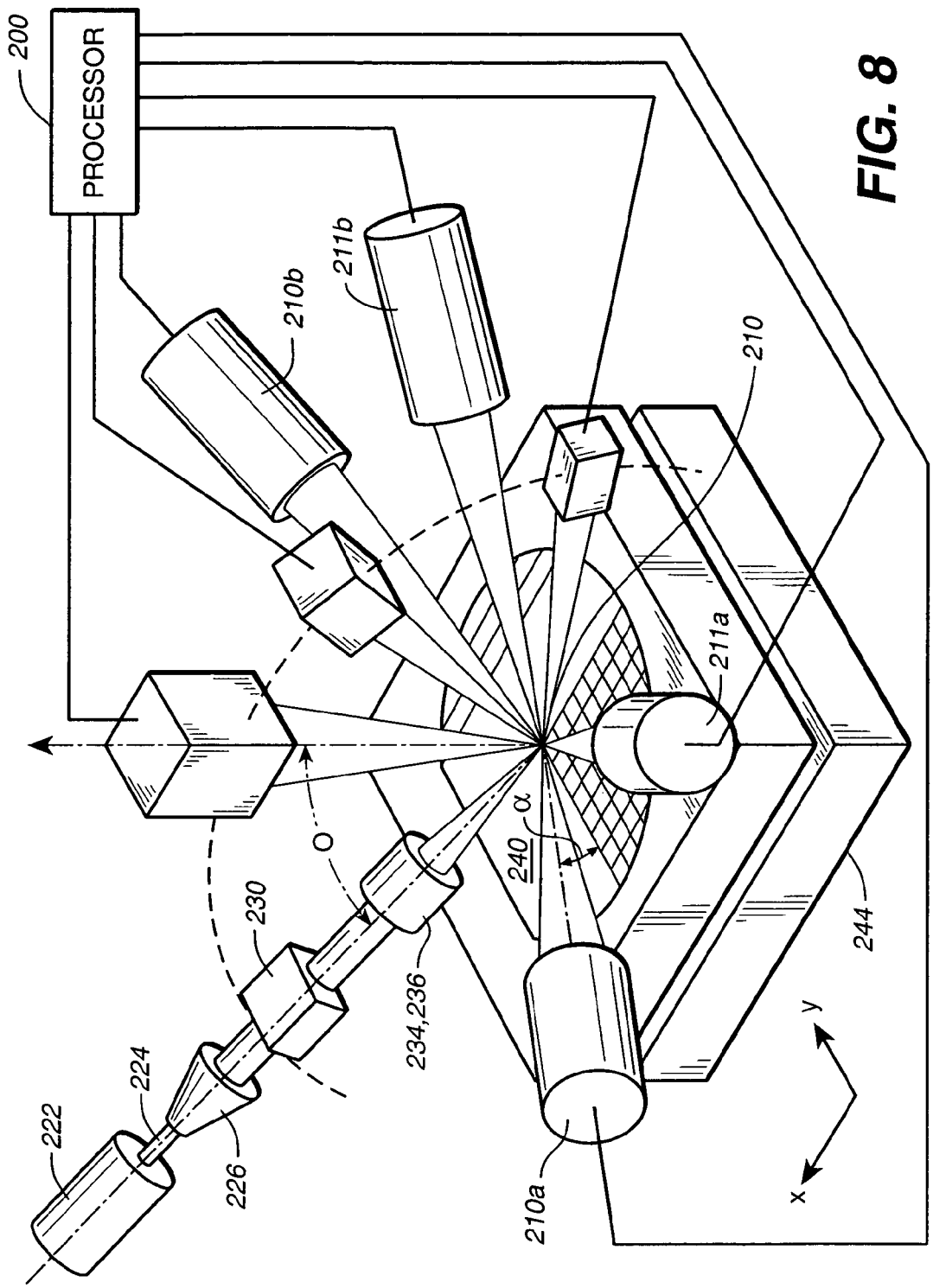
FIG. 8 is a perspective view showing in more detail the illumination and collection features of the system of FIG. 7.

FIG. 8 is a perspective view of system 220 of FIG. 7 showing in more detail the arrangement of the collection or detection channels to illustrate the preferred embodiment. As shown in FIG. 8, four collection channels and corresponding detectors are used, two channels—detectors 210a, 210b (detectors not shown separately from the collection channels in FIG. 8) for collecting scattered light that is within the respective ranges of azimuthal angles of −(75-105) degree and (75-105) degree. Two additional collection channels-detectors 211a, 211b are also employed for detecting forward scattered light that is within the respective ranges of azimuthal angles of −(30-60) degree and (30-60) degree. If desired, it is of course possible to employ four independent collection channels with other different solid angles of collection, two of said collection channels located in the forward direction to collect light in the forward direction centered substantially at ±45 degree azimuthally and two of the channels are located to collect light centered substantially at ±90 degree azimuthally. More or fewer collection channels and detectors than four can be employed as well. These channels may collect at different azimuthal and/or elevation angles.

The above-described process of achieving microview without re-scan (with or without multiperspective) can also be performed using the system of FIGS. 7 and 8. In the same manner as that described above of the microview mode without re-scan using the systems of FIGS. 1-6B, processor 200 may store in its memory the pixel intensities indicative of the scattered radiation from areas or patches of the inspected surface containing a location of a potential anomaly even though such pixel intensities do not exceed a preset threshold to indicate the presence of anomalies. In this manner, after the scan, all of the pixel intensities within the areas or patches may be viewed without having to re-scan the inspected surface 240. If desired, of course, the pixel intensities of the entire surface that is inspected may be stored. Also in the same manner as that described above, since multiple collection channels and corresponding detectors are available in the systems of FIGS. 7 and 8, it is also possible to acquire multiperspective views of areas or patches of the surface 240 that is being inspected. It is therefore possible to store the pixel intensities for all the different perspectives so that the microview capability may be performed for each one of the perspectives or for only selected ones.

Surface-to Surface (e.g. Wafer-to-Wafer) Comparison

Figure 9B:
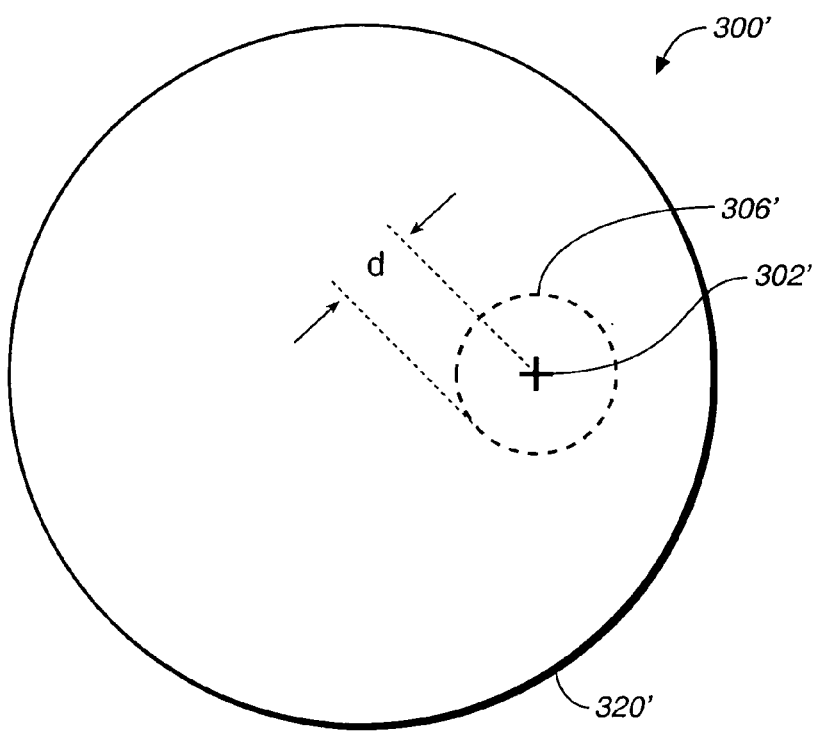
FIG. 9B is a schematic view of a surface that is inspected a surface inspection systems which, together with FIG. 9A, are useful for illustrating an aspect of the invention where the collected radiation from both surfaces in the two figures are employed for anomaly detection.

In reference to FIGS. 9A and 9B, the two surfaces 300 and 300' contain substantially the same pattern thereon. Where the two surfaces are surfaces of semiconductor wafers, such surfaces typically have alignment marks such as flats 320 and 320'. Thus the pattern on surface 300 is located relative to flat 320 at the same relative orientation and location as the orientation and location of a similar pattern on surface 300' relative to the flat 320'. Instead of using flats as alignment marks, notches (not shown) may be used instead. Thus when surface 300 is inspected by means of the optical systems in FIGS. 1-6B as well as those in FIGS. 7 and 8, the inspection system has stored in its computer such as computer 62 the relative orientations and locations of the illumination beam or beams and the collection channels relative to alignment mark 320. When surface 300' is inspected, in like manner, such system would also record the relative orientations and locations of the illumination beam or beams and the collection channels relative to the alignment mark 320'. In this manner, if surfaces 300 and 300' are inspected sequentially by the same inspection system, it is possible to be relatively certain that the area or patch 306' on surface 300' is illuminated in a manner (e.g. orientation relative to the illumination beam(s)) which is substantially the same as the illumination of patch or area 306 of surface 300. It is also possible to be relatively certain that the radiation scattered from area or patch 306' would be detected along collection directions that are substantially the same as those for collecting radiation scattered from the area or patch 306 on surface 300 in the prior scan. Areas or patches 306 and 306' are therefore corresponding patches of the two surfaces.

It is then possible to reduce noise and improve signal-to-noise ratio by taking advantage of pixel intensities for both areas or patches 306 and 306'. In one embodiment, the intensities of the pixels in area 306 may be compared to the intensities of the pixels at the same relative locations in area 306' where the comparison may be a simple subtraction. This may be performed for any two corresponding areas or patches of the two surfaces, and may indeed be performed for all of the pixels of the entire two surfaces 300 and 300'. While the above-described process is viable where surfaces 300 and 300' are inspected sequentially by the same inspection system, the same or similar advantages may also be obtained where the two surfaces are inspected by two different inspection systems, if the two surfaces are inspected in such a manner that the two corresponding areas or patches 306 and 306' compared are subject to the same illumination and collection conditions by the two different inspection systems. Then the pixel intensities at corresponding pixels in the two areas 306 and 306' may be compared or otherwise used to improve the signal-to-noise ratio in the same manner.

Figure 12:
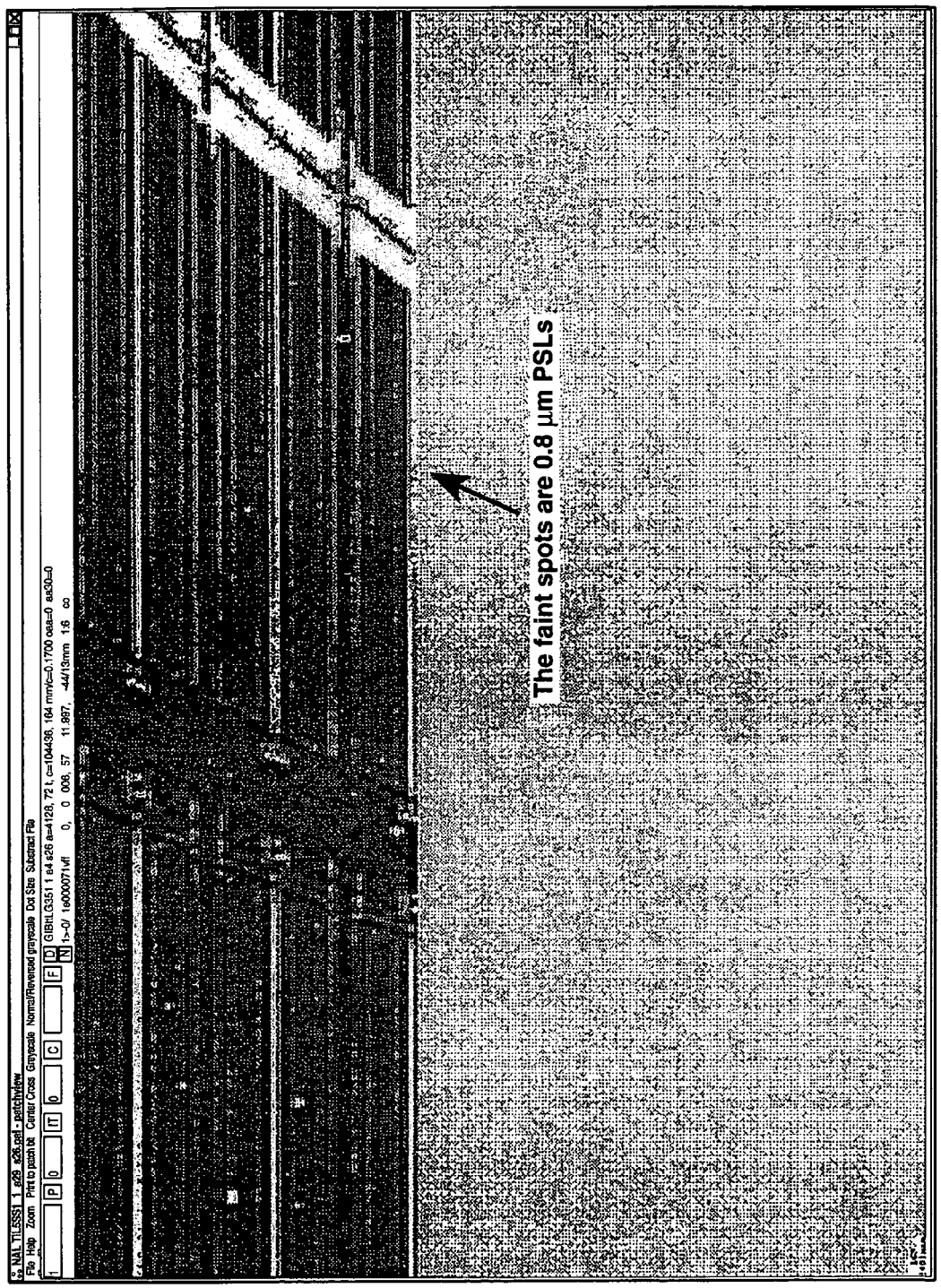
FIG. 12 is a view of radiation detected from a surface with a pattern and 0.8 micron polystyrene latex spheres thereon.

Defects of the above-described comparison are illustrated in FIGS. 12 and 13A-13D. FIG. 12 is an intensity pixel map obtained by scanning a surface with pattern and polystyrene latex (PSL) spheres of 0.8 microns diameter thereon. The white dots on plots in FIG. 12 indicate the presence of such spheres.

Figure 13A:
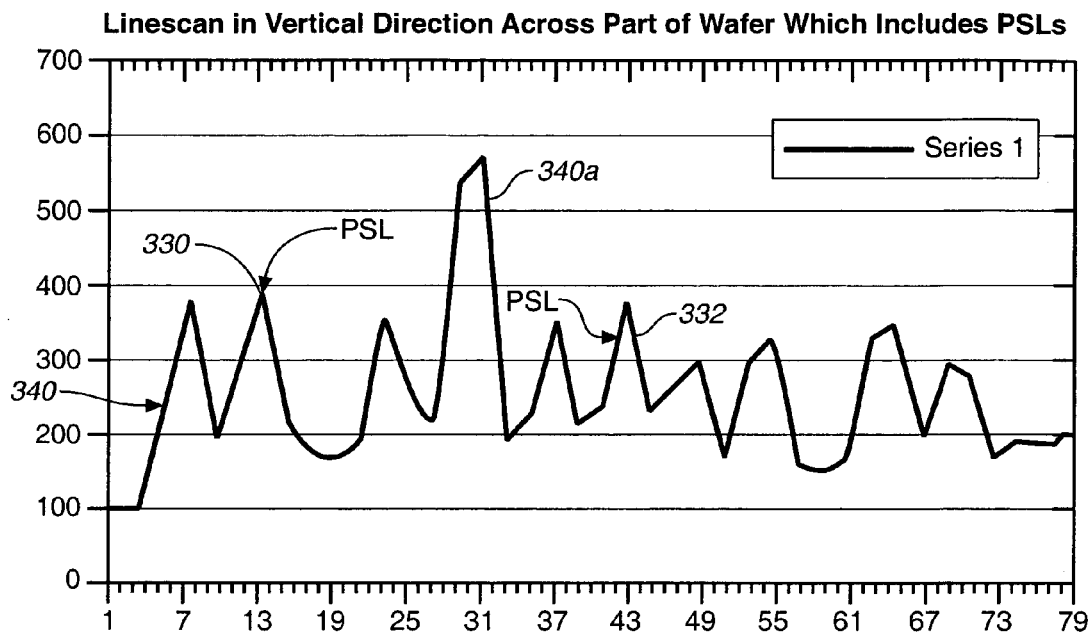
FIGS. 13A-13D are graphical plots useful for illustrating the improved performance when signals from two surfaces having the same pattern thereon are compared for defect detection on both surfaces.
Figure 13B:
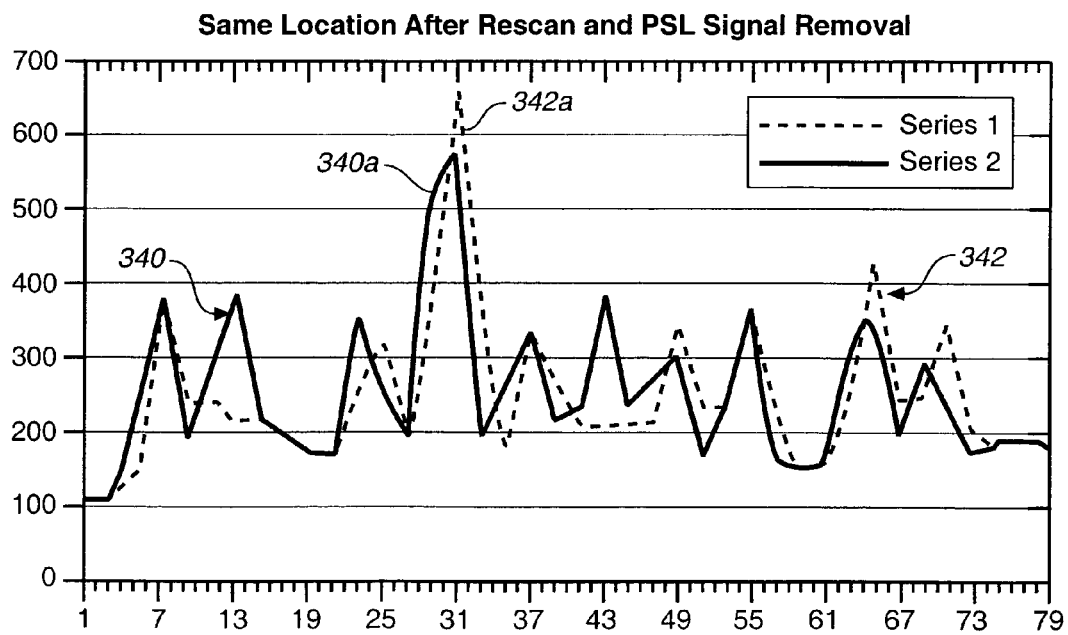

FIG. 13A is a graphical plot of the surface whose pixel map is shown in FIG. 12. In FIG. 13A, two of the peaks 330 and 332 of curve 340 have high pixel intensities indicative of the strength of radiation scattered by the PSL spheres. FIG. 13B is a graphical plot of the pixel intensities obtained when the same surface scanned to provide the plot in FIG. 13A is re-scanned after the PSL spheres have been removed, where the pixel intensities after removal is shown as curve 342. Superimposed as a thinner (compared to curve 342) line onto FIG. 13B is the curve 340 from FIG. 13A. As will be apparent from the map in FIG. 12 and a comparison of the plots in FIGS. 13A and 13B, after the PSL spheres are removed, some of the peak intensities (e.g. 330 and 332) in curve 340 do not occur in curve 342. However, curve 342 still contains high amplitude intensity pixel values, such as at 342a, which appear to overlap peak 340a of curve 340. This means that the surface that is being inspected to yield the results shown contain sources of strong scattering other than the PSL spheres, such as a pattern. For this reason, even after the PSL spheres are removed, curve 342 still contains a number of high pixel intensities.

Figure 13C:
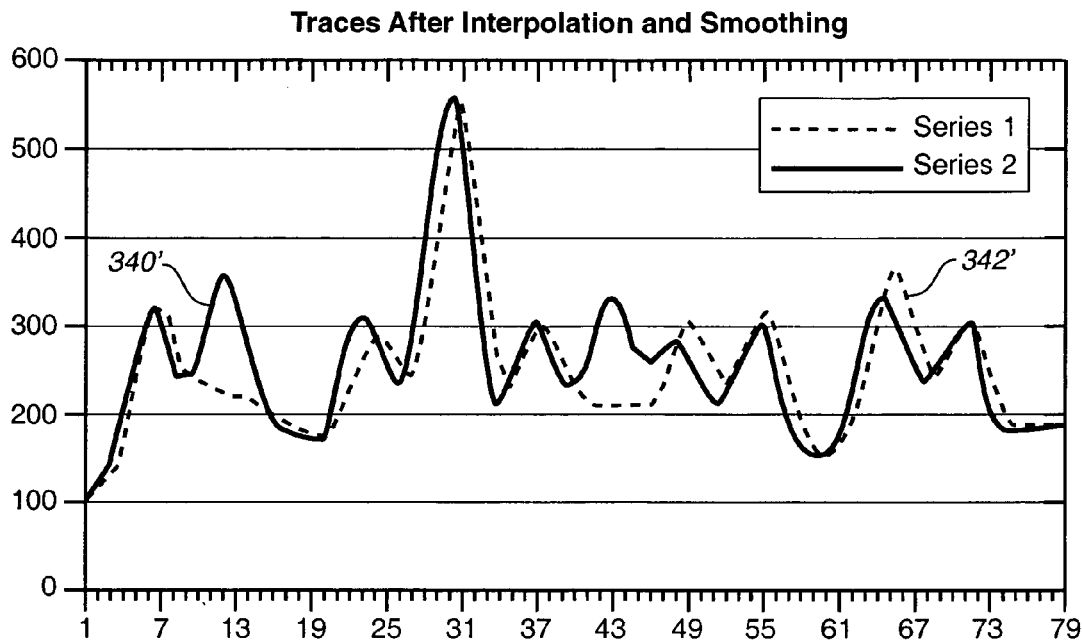
Figure 13D:
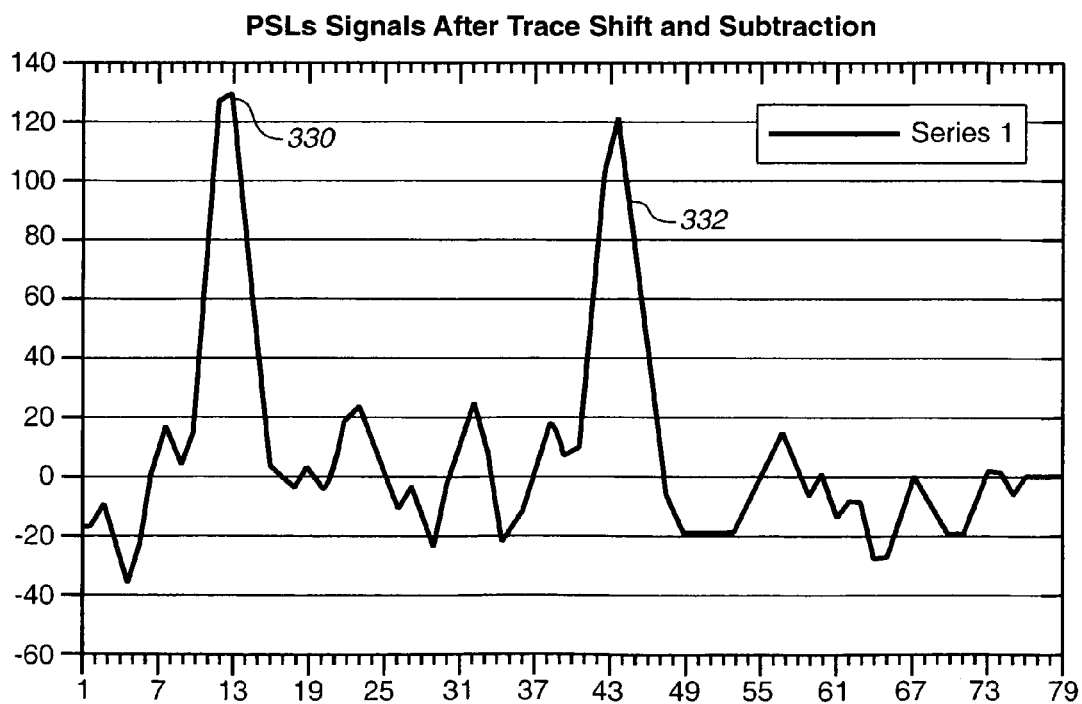

FIG. 13C is a graphical plot of the two curves shown in FIG. 13B but after pixel intensities have been processed by interpolation and smoothing where the resulting curves are indicated as 340' and 342'. As will be apparent from FIG. 13C, mere interpolation and smoothing algorithms are inadequate in reducing noise caused by strong scattering from pattern. FIG. 13D is a graphical plot of the pixel intensities that remain after the two curves 340 and 342 are shifted to overlap more exactly with one another and after the intensity values of one curve are subtracted from those of the other at the same locations of the surface. Since both curves will contain pixel values due to scattering or diffraction from the same pattern or other surface irregularities, the subtraction of pixel intensities of corresponding pixels in the two scans results in a much cleaner curve, where the pixel intensities due to the scattering from pattern or other surface irregularities are much reduced. As a result, the signal caused by the scattering from the PSL spheres becomes much more prominent and noticeable. In other words, the signal-to-noise ratio is much improved for the detection of particle defects on the surface by a comparison of the two curves 340 and 342 (e.g. by subtraction). The results illustrated in FIGS. 12-13D therefore illustrate the above described feature of the invention. The areas or patches 306 and 306' contain similar pattern or other surface irregularities, so that radiation scattered by such irregularities or pattern give rise to similar pixel intensities at the same corresponding pixel locations. By subtracting the pixel intensities of corresponding pixels in the two areas or patches, the signal-to-noise ration will be similarly increased. Obviously, comparisons other than by simple subtraction may also be used; such and other variations are within the scope of the invention.

While the invention has been described above by reference to various embodiments, it will be understood that changes and modifications may be made without departing from the scope of the invention, which is to be defined only by the appended claims and their equivalent. All references referred to herein are incorporated by reference in their entireties.

What is claimed is:

1. A surface inspection method for detecting anomalies on a surface, comprising:
    causing relative motion between a beam of radiation and the surface;
    collecting radiation scattered from the surface and directing the collected radiation to one or more channels;
    converting the collected radiation carried by at least one of the channels into respective signals;
    determining presence of potential anomalies in or on the surface from said signals;
    storing information in the signals converted from radiation scattered from locations of the surface determined to have potential anomalies and information in the signals converted from radiation scattered from portions of the surface adjacent to such locations and not determined to have potential anomalies;
    designating dimensions of an area prior to the collecting and converting, wherein the storing stores at least information in signals converted from radiation scattered from different pixels that are on the surface and that are within one or more areas of the designated dimensions, each of said areas containing a location on the surface where a potential anomaly is determined to be present; and
    erasing stored information in signals converted from radiation scattered from portions on the surface only when such portions are not within any one of the areas each containing a location on the surface where a potential anomaly is determined to be present.

2. The method of claim 1, wherein the storing stores an image of at least a portion of the surface that has not been determined to be potentially anomalous.

3. The method of claim 1, wherein the determining identifies presence of potential anomalies in or on the surface by comparing intensities of said signals to at least one threshold and said storing stores information in the signals collected from at least a portion of the surface where intensities of said signals are not more than said at least one threshold.

4. The method of claim 1, wherein the causing causes relative translational motion between a beam of radiation and the surface along two directions transverse to each other so that the beam scans substantially the entire surface.

5. The method of claim 1, further comprising retrieving the stored information and providing a map of pixels in a portion of the surface where one or more potential anomalies have been determined to be present, said pixels in the portion comprising ones at locations where presence of potential anomalies have not been determined to be present.

6. The method of claim 5, wherein the map is provided without re-scanning the surface.

7. The method of claim 1, wherein said collecting collects radiation scattered from the surface at different elevation angles from the surface or at different azimuthal angles about a line normal to the surface or about a direction corresponding thereto, so that information related to relative elevation positions from the surface or at azimuthal positions of the collected radiation about the line or is preserved, wherein said directing directs radiation scattered by the surface to a plurality of different channels so that at least some of the channels carry radiation scattered at different elevation angles or at different azimuthal angles with respect to the line, wherein the converting converts the collected radiation carried by said at least some of the channels into respective signals; and wherein said determining determines presence of potential anomalies in or on the surface from said respective signals.

8. The method of claim 7, further comprising retrieving the stored information and providing a plurality of maps of pixels in a portion of the surface where one or more potential anomalies have been determined to be present, each of the maps containing information related to the collected radiation scattered from the portion of the surface at a corresponding azimuthal angle about the line and/or elevation angle from the surface.

9. The method of claim 7, wherein the surface has a pattern thereon and wherein the determining determines by means of detectors that provide output signals in response to the collected radiation carried in the corresponding channels, and determines presence of potential anomalies without using output signals of detectors above a predetermined threshold.

10. The method of claim 7, wherein the determining determines by means of detectors that provide output signals in response to the collected radiation carried in the corresponding channels, and the determining determines presence of potential anomalies in or on the surface from a weighted average, median or minimum value of at least some of the detector output signals provided in response to the collected radiation carried in the channels from the same location of the surface.

11. The method of claim 10, wherein the storing stores information related to the weighted average, median or minimum values of the detector output signals provided in response to the collected radiation carried in the channels scattered from locations of the surface determined to have potential anomalies, and information related to the weighted average, median or minimum values of the detector output signals provided in response to the collected radiation carried in the channels scattered from portions of the surface that are determined not to have potential anomalies and that are adjacent to such locations.

12. The method of claim 1, wherein said collecting collects radiation scattered from the surface at different azimuthal angles about a line normal to the surface or about a direction corresponding thereto when the surface is scanned by the beam so that information related to relative azimuthal positions of the collected radiation about the line is preserved, wherein said directing directs radiation scattered by the surface to a plurality of different channels so that at least some of the channels carry radiation scattered at different azimuthal angles with respect to the line, wherein the converting converts the collected radiation carried by said at least some of the channels into respective signals; and wherein said determining determines presence of potential anomalies in or on the surface from said respective signals.

13. The method of claim 12, wherein the storing stores information from the respective signals so that stored information from one signal converted from collected radiation scattered from a portion of the surface at a first corresponding azimuthal angle about the line is distinguishable from stored information from another signal converted from collected radiation scattered from the same portion of the surface at a second corresponding azimuthal angle about the line different from the first corresponding azimuthal angle.

14. The method of claim 12, wherein the collecting and directing the collected radiation to channels is by means of a collector that collects the scattered radiation substantially symmetrically about the line or the direction.

15. The method of claim 1, wherein said directing comprises focusing the collected radiation to optical fibers that serve as the channels by means of at least one objective.

16. The method of claim 15, wherein said directing comprises reflecting a portion of the collected radiation at different azimuthal angles from a reflective collector towards the channels.

17. A surface inspection method for detecting anomalies on a surface, comprising:
   causing relative motion between a beam of radiation and the surface;
   collecting radiation scattered from the surface and directing the collected radiation to one or more channels;
   converting the collected radiation carried by at least one of the channels into respective signals;
   determining presence of potential anomalies in or on the surface from said signals; and
   storing information in the signals converted from radiation scattered from locations of the surface determined to have potential anomalies and information in the signals converted from radiation scattered from portions of the surface adjacent to such locations and not determined to have potential anomalies;
   setting a distance, wherein the storing stores at least information in signals converted from radiation scattered from different pixels that are on the surface and that are within such distance from any location on the surface where a potential anomaly is determined to be present; and
   erasing the stored information in signals converted from radiation scattered from a pixel on the surface only when no potential anomalies have been determined to be present within said distance from such pixel.

18. A surface inspection method for detecting anomalies on a surface, comprising:
   causing relative motion between a beam of radiation and the surface;
   collecting radiation scattered from the surface and directing the collected radiation to one or more channels;
   converting the collected radiation carried by at least one of the channels into respective signals;
   determining presence of potential anomalies in or on the surface from said signals;
   storing information in the signals converted from radiation scattered from locations of the surface determined to have potential anomalies and information in the signals converted from radiation scattered from portions of the surface adjacent to such locations and not determined to have potential anomalies;
   re-scanning portions of the surface at and adjacent to potential anomalies determined to be present by a beam of radiation;
   collecting radiation scattered from said portions of the surface during the re-scan and directing the collected radiation to each channel of a group of the channels, where the number of channels in the group is higher than the number of channels previously used for determining the presence of potential anomalies; and
   confirming or discounting presence of potential anomalies in or on the surface from signals converted from radiation carried in the group of channels.

* * * * *